United States Patent [19]

Curran et al.

[11] 4,044,138

[45] Aug. 23, 1977

[54] PHARMACEUTICAL COMPOSITIONS CONTAINING 5,6,7,8-TETRAHYDROQUINOLINE DERIVATIVES AND RELATED COMPOUNDS

[75] Inventors: Adrian Charles Ward Curran, South Cave; Roger Crossley, Reading; David George Hill, Cookham, all of England

[73] Assignee: John Wyeth & Brother Limited, Maidenhead, England

[21] Appl. No.: 625,431

[22] Filed: Oct. 24, 1975

Related U.S. Application Data

[63] Continuation-in-part of Ser. No. 600,257, July 30, 1975, which is a continuation-in-part of Ser. No. 460,265, April 11, 1974, abandoned, which is a continuation-in-part of Ser. No. 403,289, Oct. 3, 1973, abandoned.

[30] Foreign Application Priority Data

| Oct. 21, 1972 | United Kingdom | 48595/72 |
| Oct. 15, 1973 | United Kingdom | 7424/73 |
| July 21, 1973 | United Kingdom | 34866/73 |
| Aug. 16, 1973 | United Kingdom | 38701/73 |
| Oct. 17, 1973 | United Kingdom | 48595/72 |

[51] Int. Cl.$^2$ .................................. A61K 31/47
[52] U.S. Cl. ................................... 424/258
[58] Field of Search ........................ 424/258

[56] References Cited

U.S. PATENT DOCUMENTS 3,823,152   7/1974   Morimoto et al. ................ 424/258

*Primary Examiner*—Frederick E. Waddell
*Attorney, Agent, or Firm*—Arthur E. Wilfond

[57] ABSTRACT

The invention relates to pharmaceutical compositions containing 5,6,7,8-tetrahydroquinoline-8-thioamides and nitriles and related tricyclic compounds and methods of treating ulcers using said compounds.

14 Claims, No Drawings

PHARMACEUTICAL COMPOSITIONS CONTAINING 5,6,7,8-TETRAHYDROQUINOLINE DERIVATIVES AND RELATED COMPOUNDS

This application is a continuation-in-part of our co-pending application Ser. No. 600,257 filed July 30, 1975 which is a continuation-in-part of our application Ser. No. 460,265 filed Apr. 11, 1974, now abandoned, which in turn is a continuation-in-part of our Ser. No. 403,289 filed Oct. 3, 1973, and now abandoned.

The invention relates to novel pharmaceutical compositions containing novel 5,6,7,8-tetrahydroquinoline-8-thioamides and nitriles and related tricyclic compounds.

The invention provides a pharmaceutical composition comprising compound of formula I

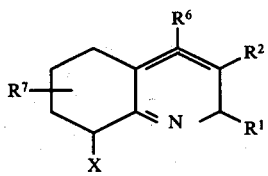

(I)

or an acid addition salt thereof with a pharmaceutically acceptable acid, wherein $R^1$, $R^2$ and $R^6$ are the same or different and are selected from hydrogen, trifluoromethyl, alkyl of 1 to 6 carbon atoms, phenylalkyl wherein the alkyl group has 1 to 6 carbon atoms, or phenyl groups, or $R^1$ and $R^2$ taken together represent an alkylene chain $—CH_2(CH_2)_n—CH_2$ wherein n is an integer from 1 to 3, $R^7$ represents hydrogen or from 1 to 3 groups selected from alkyl groups of 1 to 6 carbon atoms (which may be substituted by alkoxy of 1 to 6 carbon atoms or trifluoromethyl); phenylalkyl wherein the alkyl group has 1 to 6 carbon atoms and phenyl groups, X is cyano or $CSNHR^3$, wherein $R^3$ is hydrogen or alkyl of 1 to 6 carbon atoms and any of the phenyl groups or the phenyl portion of any phenylalkyl groups, $R^1$, $R^2$, $R^6$ and $R^7$ may be substituted by alkyl of 1 to 6 carbon atoms, alkoxy of 1 to 6 carbon atoms, halogen, nitro or trifluoromethyl, with the provisos that (1) when $R^1$ and $R^2$ or $R^2$ and $R^6$ are both alkyl they are selected from normal and secondary alkyl groups and (2) when two alkyl groups $R^7$ are present on the same carbon atom then they are both n-alkyl groups and when two $R^7$ alkyl groups are present on adjacent carbon atoms they are selected from normal and secondary alkyl groups, and a pharmaceutically acceptable carrier.

$R^7$ may be in the same position as X.

When any of $R^1$, $R^2$, $R^3$, $R^6$ or $R^7$ is an alkyl radical this is a lower alkyl radical which may have a straight or branched chain, having from 1 to 6 carbon atoms, e.g. methyl, ethyl, n-, and iso-propyl and n-, s- and t-butyl, $R^7$ may be a gem-dimethyl group and when a single radical may be on the carbon atom as the group X. The term alkyl radical is also intended to embrace cyclic alkyl radicals e.g. cyclobutyl, cyclopentyl and cyclohexyl. When any of $R^1$, $R^2$, $R^5$, $R^6$ or $R^7$ is a phenyl alkyl radical the alkyl portion may be as discussed above for an alkyl radical.

Particularly preferred compounds for use in the compositions of the invention are those in which one of $R^1$, $R^2$, $R^6$ and $R^7$ is methyl and the others are hydrogen. Compounds wherein $R^3$ is selected from hydrogen and methyl are also preferred.

Thus the present invention provides, in one preferred aspect, pharmaceutical compositions containing compounds of formula II

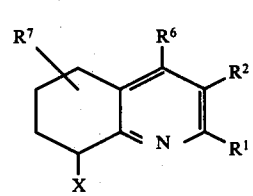

(II)

and acid addition salts thereof, wherein one of $R^1$, $R^2$, $R^6$ and $R^7$ are selected from hydrogen and methyl and X is CN, $CSNHR^3$, $R^3$ being as defined in connection with formula I. In formula II, it is preferred that X is $CSNH_2$, or $CSNHCH_3$.

In another aspect the present invention provides pharmaceutical compositions containing compounds of formula (III)

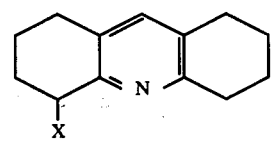

(III)

and acid addition salts thereof, wherein X is as defined in connection with formula I.

Preferably X is $CSNH_2$.

The compounds of formula I can form acid addition salt with organic acids e.g. hydrochloric, hydrobromic, sulphuric or nitric acids, or organic acids e.g. fumaric, maleic or tartaric acids. These acid addition salts may be used in the compositions of the invention.

In the compounds of formula I the carbon atom to which X is attached is asymmetric. Consequently the compounds can exist in optically active d and l forms. These optically active forms and the racemates may be used in the compositions of the invention. The optically active forms may be separated by standard techniques either by formation of an acid salt with an optically acid or by use of an optically active base with a compound in which X is COOH.

Compounds of formula I, wherein X is $CSNHR^3$, and some compounds wherein X is CN, are anit-ulcer agents which have anti-ulcer activity as determined by the method of Brodie and Hanson, J. Applied Physiology, 15, 291, 1960 or anti-secretory activity as determined by the test descrbied below. In the above test 5,6,7,8-tetrahydroquinoline-8-thiocarboxamide, 2-phenyl-, 2-t-butyl-5,6,7,8-tetrahydroquinoline-8-thiocarboxamide and 2-, 3 and 4-methyl-, 3,4-dimethyl-, 3,5-dimethyl- and 3,6-dimethyl-5,6,7,8-tetrahydroquinoline-8-thiocarboxamide have shown good activity. Compounds of formula I, wherein X is $CSNHR^3$ often display anti-secretory activity in the test of H. Shay, D. Sun and H. Greenstein, Gastroenterology 1954, 26, 906–14. For instance 5,6,7,8-tetrahydroquinoline-8-thiocarboxamide, the 2, 3 and 4-methyl and 3,6-dimethyl analogues thereof exhibited good activity in this test. Nitriles of formula I wherein X is CN are usually active in this test. Compounds which exhibit activity in the above anti-ulcer or anti-secretory tests are regarded as anti-ulcer agents.

The compounds of formula I may be prepared by various methods.

A general method of preparing the compounds of formula I comprises treating a corresponding compound in which X is hydrogen by known methods to introduce the desired group X. The compounds of formula I may be prepared from corresponding compounds of formula I wherein X is $CO_2R^5$, where $R^5$ is hydrogen or lower alkyl, where X is $CONHR^3$ or CN.

A method for preparing compounds of formula I in which X is $CO_2R^5$ comprises carboxylating a corresponding compound wherein X is hydrogen, to obtain a compound of formula I in which X is COOH or a metal salt thereof, and if desired esterifying the product with an hydroxyl compound $R^5OH$, wherein $R^5$ is as defined above, except hydrogen. The carboxylation may be achieved by preparation of a metal salt of compound of formula I wherein X is COOH, by treating a corresponding compound in which X is hydrogen, with a metal alkyl, followed by treatment of the product in situ with carbon dioxide, conveniently by bubbling $CO_2$ gas into the reaction mixture. The compound of formula I in which X is $CO_2H$ is obtained by treatment of the product, a metal salt of a compound of formula I in which X is COOH, with acid e.g. hydrochloric or hydrobromic acid. A convenient method is to treat a solution of the salt with gaseous hydrogen chloride. The metal alkyl may be one of a monovalent metal e.g. $MR^{10}$ wherein M is sodium, potassium or lithium and $R^{10}$ is alkyl, aryl or aralkyl or one of a divalent metal $M(R^{10})_2$ wherein M is calcium or magnesium. A convenient reagent $MR^{10}$ is lithium phenyl or n-butyl lithium.

It has been found that when a compound of formula I in which $R^1$ is methyl and $R^2$, $R^6$ and $R^7$ are hydrogen and X is hydrogen is carboxylated, the carboxylation may occur either on the methyl group $R^1$ or at the desired X position. Usually a mixture of desired and undesired product is formed but the desired product can be separated during subsequent work-up.

The esterification of a compound of formula I in which X is $CO_2H$ may be carried out using an hydroxyl compound $R^5OH$, wherein $R^5$ is as defined above except hydrogen according to standard procedures, e.g. in the presence of an acid catalyst e.g. some concentrated sulphuric acid or after saturation with hydrogen chloride gas or a Lewis acid e.g. boron trifluoride if desired with heat or treatment of the silver salt, (X is $COOA_g$ with an iodide $R^5I$ wherein $R^5$ is as defined above, except hydrogen.

The yield of ester can be improved by introducing a further quantity of the metal alkyl after the $CO_2$ treatment, followed by a further amount of $CO_2$. It is believed that the further quantity of metal alkyl and $CO_2$ gives the bis acid metal salt of formula IV (IV)

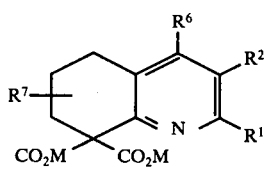

wherein $R^1$, $R^2$, $R^6$ and $R^7$ are as defined in connection with formula I and M is the metal of the metal alkyl e.g. sodium, potassium or lithium, and this salt spontaneously decarboxylates during the esterification.

A further method for preparing esters of formula I wherein X is $CO_2R^5$ comprises treating a compound of formula I as defined above wherein X is a hydrogen atom with a metal alkyl (as defined above) and then treating the product with a haloformate of formula $HalCOOR^5$ wherein Hal is a halogen atom e.g. chlorine or bromine and $R^5$ is as defined above. The product is usually a mixture of the desired compound of formula I wherein X is $CO_2R^5$ and the corresponding bis-ester of formula V (V)

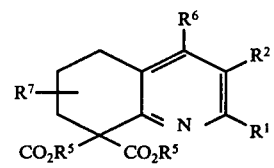

These bis-esters are useful for preparing the corresponding compounds of formula I wherein X is $CO_2H$. We have found that this mixture of mono and bis-esters can be converted directly to the corresponding compound of formula I where X is $CO_2H$, by saponification with an alkali or alkaline earth metal hydroxide to give a mixture of the metal salt of the mono acid of formula I wherein X is $CO_2H$ and the metal salt of the diacid of formula V wherein $R^5$ is H. Treatment of this mixture with a mineral acid e.g. hydrochloric acid gives the desired acid of formula I wherein X is $CO_2H$ since the diacid spontaneously decarboxylates to form the mono acid.

The product of the haloformate reaction may be treated with a further quantity of the metal alkyl followed by a further quantity of the haloformate thereby producing more of the bis-ester (V).

A further method for preparing compounds of formula I in which X is $CO_2H$ comprises decarboxylation of a compound of formula V

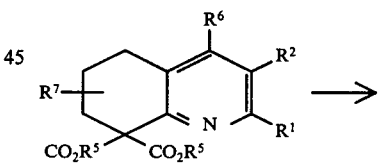

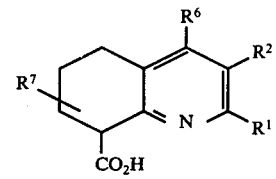

wherein $R^1$, $R^2$ and $R^5$ are as previously defined. The decarboxylation can be carried out by heating the dicarboxylic acid of formula V wherein $R^5$ is hydrogen. Usually the dicarboxylic acid is prepared in situ by hydrolysis of the corresponding di-ester, wherein $R^5$ is as defined above except hydrogen. The hydrolysis and decarboxylation may be carried out by heating with a dilute mineral acid e.g. HCl or sulphuric acid or the diester may be saponified with alkali e.g. sodium or potassium hydroxide. The resulting salt is then acidified and decarboxylated by heating.

Compounds of formula I, in which X is CONHR³ may be prepared by treatment of a corresponding compound of formula I wherein X is COCl or CO₂R⁵ and R⁵ is as defined above, except hydrogen, with ammonia to give a compound of formula I in which X is CONH₂, which may be subsequently alkylated to introduce the group R³ wherein R³ is as defined above except hydrogen. Conveniently a compound of formula I wherein X is CO₂R⁵ wherein R⁵ is lower alkyl, especially methyl or ethyl, is treated with ammonia. Alternatively substituted amides of formula I wherein X is CONHR³ and R³ is other than hydrogen may be prepared by treatment of the carboxylic ester of formula I wherein X is CO₂R⁵ and R⁵ is other than hydrogen with an amine of formula R³NH₂ wherein R³ is as defined previously except hydrogen. The substituted amides may conveniently be prepared from the acid chloride of formula I wherein X is COCl by treatment with a primary amine R³NH₂.

An example of a primary amine which may be used in the above reactions is methylamine.

The acid chlorides may be prepared by treatment of the corresponding acid of formula I, wherein X is CO₂H with thionyl chloride, phosphorus oxychloride or phosphorus pentachloride.

A further process for preparing compounds of formula I as defined above wherein R¹ and R² are as defined above and X is CONHR³ wherein R³ is hydrogen or alkyl, comprises treating an ester compound of formula I, wherein X is CO₂R⁵ and R⁵ is alkyl with an amide of formula R⁹CONHR³ or a salt thereof wherein R³ is hydrogen or alkyl and R⁹ is hydrogen or lower alkyl in the presence of an alkali-metal alkoxide.

Preferably a molar equivalent of alkali-metal alkoxide is used for each mole of ester of formula I. The alkali-metal alkoxide may be one derived from a lower alkanol having from 1 to 6 carbon atoms e.g. methanol or ethanol. The alkali-metal is preferably sodium.

The ester of formula I is preferably a lower alkyl ester.

The amide R⁹CONHR³ is preferably one in which R⁹ is hydrogen or methyl. R³ is also preferably hydrogen or methyl. Thus preferred amides are formamide, N-methylformamide, acetamide and N-methylacetamide. Salts, especially alkali-metal salts of these amides may be used as starting materials.

The reaction may be carried out by heating the reactants together.

The amides of formula I, wherein X is CONH₂ may also be prepared by partial hydrolysis of the corresponding nitriles of formula I, wherein X is CN. This hydrolysis may be accomplished in conventional manner e.g. by concentrated (e.g. 96%) sulphuric acid.

Thioamides of formula I wherein X is CSNHR³ wherein R³ is as already defined may be preapred by treatment of the corresponding compounds in which X is CONHR₃ with P₂S₅ e.g. by refluxing in pyridine. As mentioned below when the starting material is one in which X is CONH₂, decomposition to the nitrile may occur. We have found that this decomposition can be avoided by conducting the P₂S₅ reaction in the presence of H₂S. Alternatively the thioamides may be prepared by treatment of a nitrile of formula I, wherein X is CN with H₂S to give the unsubstituted thioamide wherein X is CSNH₂. Substituted thioamides may be obtained by conducting this reaction in the presence of a primary amine R³NH₂ wherein R³ is as defined above except hydrogen. The H₂S reaction can be carried out in a suitable solvent in the presence of a catalyst such as a tertiary amine e.g. a trialkylamine such as triethylamine.

Substituted thioamides may also be prepared by treatment of an unsubstituted thioamide of formula I, wherein X is CSNH₂ with an amine of formula R³NH₂ wherein R³ is as previously defined and is other than hydrogen, in the presence of H₂S. The amine may be a mono alkylamine e.g. methylamine. The nitriles of formula I wherein X is CN, may be prepared by dehydration of the corresponding amides of formula I wherein X is CONH₂. Such dehydration can be carried out with P₂O₅ as the dehydrating agent. Other dehydrating agents are phosphorus pentachloride or thionyl chloride. It has also been found that this decomposition can be effected with P₂S₅ and this is believed to be a novel reaction per se. The decomposition with P₂S₅ has been observed as a side reaction during the conversion of the amides of formula I wherein X is CONH₂ to the corresponding thioamides wherein X is CSNH₂ using P₂S₅. The nitrile can either be separated, e.g. by chromatography or the mixture treated with H₂S for conversion of the nitrile to the corresponding thioamide. The dehydration may also be effected by heating the amide in hexamethylphosphorictriamide as solvent. When using this solvent it has been found that a compound of formula I in which X is CONMe₂ may be formed as a significant by-product. The latter is also believed to be a novel reaction per se.

A further method for preparing the thioamides of formula I, wherein X is CSNH₂ comprises reacting a nitrile of formula I wherein X is CN with a thioamide of formula R⁸CSNH₂ where R⁸ is an alkyl group, e.g. a lower-alkyl group of 1-6 carbon atoms, preferably a methyl group, in a suitable solvent such as dimethyl formamide saturated with hydrogen chloride.

The starting compounds of formula I wherein X is hydrogen, used in the above mentioned carboxylation reaction may be prepared by cyclisation of a compound of formula VI in the presence of hydroxylamine

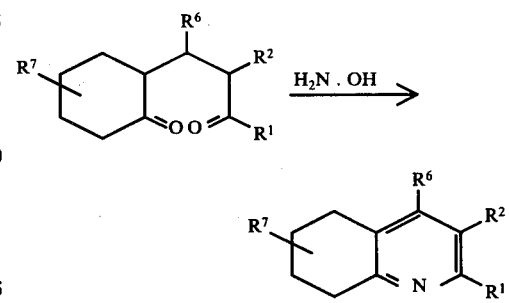

(VI)

wherein R¹ and R² are as defined above but R¹ is preferably other than hydrogen and R⁶ and R⁷ are as defined above. Starting compounds of formula I, when X is hydrogen, R¹ is hydrogen and R⁷ is hydrogen, or if not hydrogen is not on the 5-position may be prepared by reduction of the corresponding 5-oxo compound (VII) using a reducing agent which does not affect the unsaturation of the fused pyridine ring e.g. hydrazine i.e. a Wolff-Kishner reduction.

(VII)

-continued

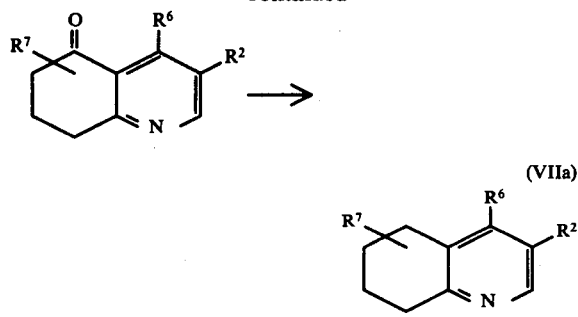

(VIIa)

The starting material of formula (VII) wherein $R^2$ and $R^6$ are hydrogen may be prepared by the following scheme:

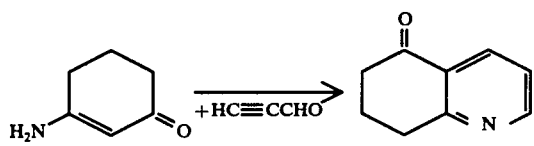

The reaction can be carried out in a suitable solvent e.g. dimethylformamide at room temperature followed by distillation of the products.

Compounds of formula (I) wherein X is hydrogen, $R^1$ is hydrogen and $R^2$ is other than hydrogen may be prepared by known methods.

The compounds of formula VI (wherein $R^7$ is hydrogen or is not on both positions adjacent the oxo group) may be prepared by one of the following schemes:

A)

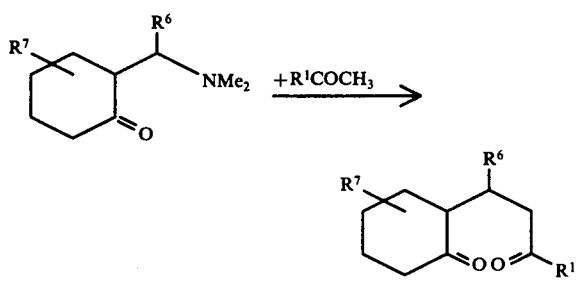

B)

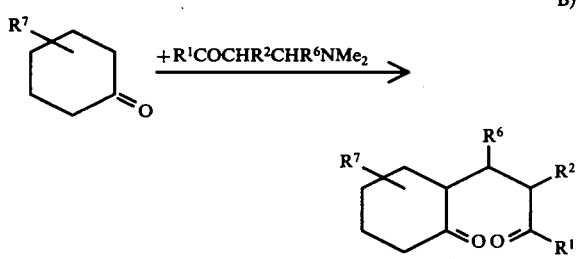

wherein $R^1$, $R^2$, $R^6$ and $R^7$ are as defined above, $R^1$ being other than hydrogen. The reactants used are known compounds or may be prepared by methods known for analogous compounds.

Other compounds for preparing starting compounds of formula I wherein X is hydrogen are described in the literature e.g. Breitmaier & Bayer Tetrahedron Letters No. 38, 1970, 3291–3294, which gives methods for preparing compounds in which X is hydrogen and $R^1$ and $R^2$ are hydrogen and X is hydrogen and $R^2$ is alkyl.

For the pharmaceutical carrier in the compositions of the invention any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, enulsions, syrups and elixirs. The active ingredient can be dissolved or suspended in a pharmaceutically acceptable sterile liquid carrier, such as sterile water, sterile organic solvent or a mixture of both. The active ingredient can often by dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The ati-ulcer compositions of the invention will be administered orally in either liquid or solid composition form. These compositions may include one or more antacid ingredients e.g. aluminium hydroxide, magnesium hydroxide or bismuth carbonate, aluminium glycinate, calcium carbonate magnesium trisilicate, sodium bicarbonate or the alumina gel described in British Specification No. 1,284,394. The following Examples illustrate the invention; all temperatures are in ° C.

EXAMPLE 1

A. 2-Phenyl-5,6,7,8-tetrahydroquinoline 2-(3'-Phenyl-3'-oxopropyl)cyclohexanone was prepared according to the method of W. Hahn and J. Epsztain (Roczniki Chem. 1963, 37, 403–12): A mixture of β-dimethylaminopropiophenone (27 gm.) amd cyclohexanone (37.5 g.) were heated at reflux for 5 hours under nitrogen and the solvent removed in vacuo. The residual oil was distilled giving 2-(3'-phenyl-3'-oxopropyl)cyclohexanone (14 g.) which was cyclised to the title compound according to the method of Hahn and Epsztain by dissolving the diketone (12 g.) in ethanol (65 ml.), treating with hydroxylamine hydrochloride (9 g.) and heating under reflux for 1 hour. The cooled reaction mixture was poured onto water (300 ml.), extracted with ether (2 × 50 ml.) and the extracts discarded. The aqueous solution was made basic with $K_2CO_3$ and extracted with ether (3 × 50 ml.). The combined ether extracts were dried and the solvent removed in vacuo. The residual oil was distilled to give the title compound as a colourless oil (7 g.) b.p. 134°–8° C/15 mm. Found: C, 85.40; H, 7.5; N, 6.9%, $C_{15}H_{15}N$ requires: C, 86.00; H, 7.2; N, 6.7%.

B. Methyl-2-phenyl-5,6,7,8-tetrahydroquinoline-8-carboxylate

A solution of 2-phenyl-5,6,7,8-tetrahydroquinoline (20 g.) in ether (50 ml.) was added dropwise over 30 mins. to a preformed ethereal solution of phenyllithium (prepared from bromobenzene (40 g.) and lithium (2.78 g.) in dry ether (160 ml.). The reaction mixture was stirred for 1 hour at room temperature and treated with dry $CO_2$ gas until the colour was discharged. The solvent was removed in vacuo and the residue dissolved in ethanol saturated with dry HCl gas (250 ml.) and the solid filtered and recrystallised from water giving 2-phenyl-5,6,7,8-tetrahydroquinoline-8-carboxylic acid hydrochloride (12 g.). This was dissolved in methanol (200 ml.) and the solution treated with dry HCl gas whilst heating at reflux for 4 hours. The solvent was removed in vacuo and the residue dissolved in water (50 ml.), made with 2N NaOH and extracted into chloroform (3 × 100 ml.). The combined extracts were dried, evaporated to dryness and the residual solid recrystallised from petroleum ether giving the title compound as colourless needles (11 g.) mp 75° C. Found: C, 76.8; H, 6.5; N, 5.14; $C_{17}H_{17}NO_2$ requires: C, 76.4; H, 6.4; N, 5.2%.

EXAMPLE 2

2-Phenyl-5,6,7,8-Tetrahydroquinoline-8-carboxamide

Methyl-2-phenyl-5,6,7,8-tetrahydroquinoline-8-carboxylate (4 g.) was dissolved in methanol previously saturated with ammonia (90 ml.) and heated in a bomb at 100° C for 4 days. Removal of the solvent in vacuo gave an oily solid which on recrystallisation from ethyl acetate gave the title compound as colourless needles (1.5 g.) mp 145° C. Found: C, 76.4; H, 6.5; N, 11.1% $C_{16}H_{16}N_2O$ requires: C, 76.2; H, 6.4; N, 11.1%.

EXAMPLE 3

2-Phenyl-5,6,7,8-tetrahydroquinoline-8-thiocarboxamide

2-Phenyl-5,6,7,8-tetrahydroquinoline -8-carboxamide (8 g.) was dissolved in pyridine (20 ml.), treated with $P_2S_5$ (5.2 g.) and the mixture heated at reflux temperature for 30 minutes. The solvent was removed in vacuo and the residual oil dissolved in dilute HCl, washed with ether (2 × 50 ml.) and the washings discarded. The aqueous solution was made basic, extracted into chloroform (3 × 50 ml.) and the combined extracts dried and evaporated to dryness. The residual oil was chromatographed on silica gel by elution with chloroform giving 8-cyano-2-phenyl-5,6,7,8-tetrahydroquinoline (1.2 g.) as colourless needles from ether mpt. 100° C. Found: C, 82.0; H, 6.2; N, 11.7% $C_{16}H_{14}N_2$ requires: C, 82.0; H, 6.0; N, 11.9%. Further elution with chloroform gave the title compound (1.1 g.) as colourless needles from ether mpt. 154° C. Found: C, 71.8; H, 6.1; N, 10.2%, $C_{16}H_{16}N_2S$ requires: C, 71.6; H, 6.0; N, 10.4%.

EXAMPLE 4

N,N-Dimethyl-2-phenyl-5,6,7,8-tetrahydroquinoline-8-carboxamide

2-Phenyl-5,6,7,8-tetrahydroquinoline-8-carboxamide (6 g.) was dissolved in hexamethylphosphorictriamide (24 ml.) and the solution heated at 220° C for 2 hours. The cooled reaction mixture was poured onto water (50 ml.), extracted with chloroform (3 × 100 ml.) and the combined extracts washed with water (3 × 100 ml.), dried and evaporated to dryness. The residual oil was chromatographed on silica gel by elution with chloroform giving 2-phenyl-8-cyano-5,6,7,8-tetrahydroquinoline (2.5 g.) recrystallised from ether as colourless needles mpt. 100° C. Further elution with chloroform gave N,N-dimethyl-5,6,7,8-tetrahydroquinoline-8-carboxamide (1.1 g.) which recrystallised from ether as colourless needles mpt. 140° C. Found: C, 77.17; H, 7.22; N, 10.24%. $C_{18}H_{20}N_2O$ requires: C, 77.11; H, 7.19; N, 9.99%.

EXAMPLE 5

2-Phenyl-5,6,7,8-tetrahydroquinoline-8-thiocarboxamide

2-Phenyl-8-cyano-5,6,7,8-tetrahydroquinoline (2 g.) was dissolved in pyridine (5 ml.) and triethylamine (1.3 ml.) and the solution treated with $H_2S$ gas for 6 hours and the reaction mixture allowed to stand at room temperature for 12 hours. The solvent was removed and the residual oil dissolved in dilute HCl, extracted with ether (2 × 50 ml.) and the extracts discarded. The aqueous solution was made basic and extracted into chloroform (3 × 50 ml.). The combined extracts were dried and evaporated in vacuo to give 2-phenyl-5,6,-7,8-tetrahydroquinoline-8-thiocarboxamide which was dissolved in ethanol (5 ml.), diluted with ether (25 ml.) and the solution saturated with HCl gas. The solvent was removed in vacuo and the residual solid recrystallised from methanol-ether giving hydrochloride of the title compound as colourless needles mpt. 211° C. Found: C, 63.41; H, 5.70; N, 8.94%. $C_{16}H_{16}N_2S \cdot HCl$ requires: C, 63.04; H, 5.62; N, 9.19%.

EXAMPLE 6

A. 5,6,7,8-Tetrahydroquinoline

5-Oxo-5H-6,7,8-trihydroquinoline was prepared according to the method of F. Zymalkawski (Arch. Chem. 1961, 294, 759) by adding propiolaldehyde (16 g.) to a solution of 3-aminocyclohex-2-enone (31 g.) in DMF (150 ml.) over 5 mins. When the exothermic reaction had ceased, the flask was fitted for downward distillation and the reaction mixture heated at 100° C under a vacuum of 15 mm. and the distillate collected and discarded. The temperature was raised to 160°–170° collecting the distillate which was dissolved in dilute HCl (75 ml.) and extracted with ether (2 × 50 ml.). The combined ethereal extracts were discarded. The aqueous solution was made basic and extracted with ether (3 × 150 ml.) and the combined ethereal extracts dried and evaporated in vacuo. The residual oil was distilled giving 5-oxo-5H-6,7,8-trihydroquinoline (21 g.) b.p. 133°–4° C/15 mm. which was dissolved in diethylene glycol (190 ml.) and treated with hydrazine hydrate (14 g.) and sodium hydroxide (14 g.). The reaction mixture was heated at reflux for 30 minutes and then for 3½ hours under a Dean and Stark water separator. The cooled reaction mixture was poured onto water (100 ml.), extracted with ether (3 × 100 ml.) and the combined extracts dried and evaporated in vacuo. The residual oil was distilled giving the title compound as a colourless oil (10 g.) b.p. 100°–5° C/15 mm.

B. Methyl-5,6,7,8-tetrahydroquinoline-8-carboxylate

A solution of 5,6,7,8-tetrahydroquinoline (14 g.) in dry ether (100 ml.) was added dropwise over ½ hour to an ethereal solution of phenyl lithium (prepared from bromobenzene (42 g.) and lithium (3.7 g.) in dry ether (300 ml.) and the reaction mixture stirred at room temperature for a further one hour. The cooled reaction mixture was saturated with dry $CO_2$ gas, evaporated in vacuo and the residue treated with methanol previously saturated with dry HCl (500 ml.) and the solution heated at reflux for 12 hours. The solvent was removed in vacuo and the residue dissolved in water (50 ml.), extracted with ether (3 × 150 ml.) and the extracts discarded. The aqueous solution was made basic and extracted with ether (3 × 100 ml.). The combined ethereal extracts were dried, evaporated in vacuo and the residual oil distilled giving methyl-5,6,7,8-tetrahydroquinoline-8-carboxylate as a colourless oil (13 g.) b.p. 92° C/0.05 mm. The hydrochloride was prepared by saturating an ethereal solution with dry HCl gas and recrystallising the resultant solid from methanol-ether to give the hydrochloride of the title compound as colourless needles mpt. 173° C. Found: C, 58.2; H, 6.3; N, 6.3%. $C_{11}H_{13}NO_2 \cdot HCl$ requires C, 58.0; H, 6.2; N, 6.1%.

EXAMPLE 7

5,6,7,8-Tetrahydroquinoline-8 -crboxamide

Methyl-5,6,7,8-tetrahydroquinoline-8-carboxylate (9 g.) was dissolved in methanol previously saturated with ammonia (270 ml.) and heated in a bomb at 100° C for 5 days. The solvent was removed and the residual oil triturated with hot petroleum ether (40°–60°). The resultant solid was filtered and then recrystallised from ethylacetate giving the title compound as colourless needles mpt. 132° C (5 g.). Found: C, 67.7; H, 7.1; N, 16.0% $C_{10}H_{12}N_2O$ requires: C, 68.1; H, 6.9; N, 15.9%.

EXAMPLE 8

5,6,7,8-Tetrahydroquinoline-8-thiocarboxamide

A solution of 5,6,7,8-tetrahydroquinoline-8-carboxamide (1.2 g.) in pyridine (15 ml.) was treated with $P_2S_5$ (0.8 g.) and the mixture heated at reflux for 30 mins. The solvent was removed in vacuo and the residual oil treated with 2N NaOH (5 ml.) and saturated with solid $K_2CO_3$ and extracted into chloroform (3 × 50 ml.). The combined extracts were dried and the solvent removed in vacuo. The residual oil was dissolved in pyridine (4 ml.) and triethylamine (1 ml.) and the solution saturated with $H_2S$ (6 hours) and allowed to stand overnight. Removal of the solvent gave a solid (850 mgs.) which was recrystallised from methanol giving the title compound as the quarter hydrate, colourless needles m.p. 160° C. Found: C, 59.8; H, 6.2; N, 14.0%. $C_{10}H_{12}N_2S \cdot \frac{1}{4}H_2O$ requires: C, 59.6; H, 6.4; N, 13.9%.

The UV, IR and NMR Spectra of the title compound were determined:

1. UV Spectrum in 95% EtOH (1.07 mg. in 100 ml.)
   Max 272 nm, E13,300
2. IR Spectrum
   3230 cm$^{-1}$)
   3060 cm$^{-1}$) $NH_2$ stretch
   1660 cm$^{-1}$   —$NH_2$ deformation or/and C=CN stretch
   1575 cm$^{-1}$   C=C stretch
   1500–900 cm$^{-1}$ 'fingerprint region'; numerous bands caused by complex and coupled vibrations. Two bands are particularly prominent 1280 cm$^{-1}$ and 1020 cm$^{-1}$
   802 cm$^{-1}$)   =CH deformation, characteristic of 2,3-
   720 cm$^{-1}$)   disubstituted pyridine.
3. NMR Spectrum - in $d_6$ DMSO (100 MH$_2$)

| | | | |
|---|---|---|---|
| δ1.5–2.3 | broad multiplet | 4 protons | $CH_2$-6 and 7 |
| δ2.7 | multiplet | 2 protons | $CH_2$-5 |
| δ4.15 | triplet (J=7Hz) | 1 proton | CH-8 |
| δ7.08 | quartet | 1 proton | H-3 |
| δ7.44 | quartet | 1 proton | H-4 |
| δ8.29 | quartet | 1 proton | H-2 |
| δ9.25 and 9.45 | broad doublet | 2 protons | $NH_2$ |

Coupling constants = $J_{23}$ = 5Hz, $J_{24}$ = 1.5 Hz, $J_{34}$ = Hz

It is indicated in the index to Chemical Abstracts that 5,6,7,8-tetrahydroquinoline-8-thiocarboxamide is disclosed in Z. Naturforch. 6b 147–155 (1951), however, the actual abstract does not disclose the compound and examination of the paper reveals that the index is in error since the compound actually disclosed is 8-quinoline thiocarboxamide, the benzene ring of which has been shown without the unsaturation being marked in accordance with a custom then in use, see Organic Chemistry, Paul Karrer, 4th English Edition, Elsevier, 1950 eg. at page 813.

EXAMPLE 9

A. 2-t-Butyl-5,6,7,8-tetrahydroquinoline

5-Dimethylamino-2,2-dimethylpentan-3-one hydrochloride (100 g.), prepared from pinacolone according to the method of Casey & Ison (Tetrahedron, 1969, 25, 641–6) was dissolved in water (50 ml.) and the pH adjusted to 12.0 with 10N NaOH and extracted with ether (3 × 50 ml.). The combined ethereal extracts were dried (MgSO4), evaporated in vacuo and the residual oil dissolved in cyclohexanone (300 ml.). The mixture was heated at reflux temperature for 8 hours and then cooled. The reaction mixture was then distilled at 15 mm. to remove excess cyclohexanone and than at 1 mm. to give 2(3'-t-butyl-3'-oxopropyl)cyclohexanone (82 g.) which was dissolved in ethanol (275 ml.) and treated with hydroxylamine hydrochloride (70 g.). The mixture was heated at reflux temperature for 2 hours as described in the general method of W. Hahn and J. Epsztain (Roczniki Chem. 1963, 37, 403–12). The solvent was removed in vacuo and the residual oil dissolved in ether (100 ml.) The ethereal solution was washed with dilute HCl (3 × 20 ml.) and discarded. The aqueous solution was made basic with 2N NaOH and extracted with ether (3 × 50 ml.) and the combined extracts dried and evaporated in vacuo. The residual oil was distilled giving the title compound as a colourless oil b.p. 80°–6°C/1 mm. (yield 47 g., 64%).

B. 2-t-Butyl-5,6,7,8-tetrahydroquinoline-8-carboxamide

Methyl-2-t-butyl-5,6,7,8-tetrahydroquinoline-8-carboxylate was prepared from 2-t-butyl-5,6,7,8-tetrahydroquinoline (18.9 g., 0.1 m). and phenyl lithium (0.1 m.)

by the general method described in Example 1B and was isolated as a pale yellow oil (9 g.) b.p. 106° C/0.4 mm.

The title compound was prepared from methyl-2-t-butyl-5,6,7,8-tetrahydroquinoline-8-carboxylate (8 g.) by the general method described in Example 2 and was isolated as colourless needles (3 g.) after recrystallisation from n-hexane m.p. 131° C. Found: C, 72.06; H, 8.71; N, 11.62%. $C_{14}H_{20}N_2O$ requires: C, 72.38; H, 8.68; N, 12.06%.

EXAMPLE 10

2-t-Butyl-5,6,7,8-tetrahydroquinoline-8-thiocrboxamide

The title compound was prepared from 2-t-butyl-5,6,7,8-tetrahydroquinoline-8-carboxamide (4 g.) and $P_2S_5$ (3 g.) as described in Example 8 and was isolated as creamy needles after recrystallisation from n-hexane m.p. 126° C (650 mgs.). Found: C, 68.18; H, 8.25; N, 11.14%. $C_{14}H_{20}N_2S$ requies C, 67.70; H, 8.12; N, 11.23%

EXAMPLE 11

5,6,7,8-Tetrahydroquinoline

3-Methoxyacrolein was prepared from 1,1,3,3-tetramethoxypropane (Helv. Chim. Acta 1959, 42, 851) and converted to 3-aminoacrolein according to the method of Brietmaier and Gasenmann (Chem. Ber. 1971, 104, 665–7). 5,6,7,8-Tetrahydroquinoline was prepared from 3-aminoacrolein as described by Brietmaier and Bayer (Tet. Letts 1970, 38, 3291). A mixture of 3-aminoacrolein (7.3 gm, 0.1 m) and cyclohexanone (12 gm., 0.12m) was treated with triethylamine (5 ml.) and piperidinium acetate (0.1 gr) and the mixture heated in an oil bath at 120° for 24 hours. The cooled reaction mixture was dissolved in ether (100 ml.), washed with water and 2N HCl (2 × 20 ml.) and the acid washings combined, made basic with sodium carbonate and extracted with ether. The combined extracts were dried, evaporated and the residue distilled to give the title compound as a pale yellow. oil (4.5 gm, 35%) b.p. 100°/15 mm.

EXAMPLE 12

2-Methyl-5,6,7,8-tetrahydroquinoline

4-Diethylaminopropan-2-one prepared from acetone and diethylamine (J.C.S. 1937, 53) was reacted with cyclohexanone by the general method described in C.A. 72, 132478h to give 2(3¹-methyl-3¹-oxopropyl) cyclohexanone as a colourless oil b.p. 150°/20 mm.

The title compound was prepared from 2(3¹-methyl-3¹-oxopropyl)cyclohexanone according to the general method described in Examples 1 and 9A and isolated as a colourless oil b.p. 116°–20°/18 mm. (60% yield).

EXAMPLE 13

2l -Methyl-5,6,7,8-tetrahydroquinoline-8-carboxamide

Reaction of 2-methyl-5,6,7,8-tetrahydroquinoline with phenyl lithium and carbon dixoide followed by esterification according to the general method described in Examples 1B and 6B gave an inseparable mixture of methyl-2-methyl-5,6,7,8-tetrahydroquinoline-8-carboxylate and methyl 5,6,7,8-tetrahydroquinoline-2-acetate which was converted without purification to a mixture of 2-methyl-5,6,7,8-tetrahydroquinoline-8-carboxamide and 5,6,7,8-tetrahydroquinoline-2-acetamide by reaction with ammonia using the method described in Example 2. Fractional recrystallisation from diisopropyl ether gave the title compound as colourless needles m.p. 114° (overall yield 30%) (Found: C, 69.31, H, 7.45, N, 14.7, $C_{11}H_{14}N_2O$ requires: C, 69.45, H, 7.42; N, 14.72%).

EXAMPLE 14

2-Methyl-5,6,7,8-tetrahydroquinoline-8-thiocarboxamide

2-Methyl-5,6,7,8-tetrahydroquinoline-8-carboxamide was treated with $P_2S_5$ to give 2-methyl-8-cyano-5,6,7,8-tetrahydroquinoline which was treated with $H_2S$ (both reactions being carried out by the method described in Example 8 to give the title compound as colourless needles from ethylacetate (28%) m.p. 98° (Found: C, 64.32; H, 6.93; N, 13.52%, $C_{11}H_{14}N_2S$ requires: C, 64.04; H, 6.84; N, 13.58%).

EXAMPLE 15

3-Methyl-5,6,7,8-tetrahydroquinoline

The title compound was prepared from commercially available 3-amibo-2-methylacrolein and cyclohexanone according to the method of Breitmaier and Bayer (Tet. Letts. 1970, 38, 3291–4) and isolated as a pale yellow oil b.p. 120°/15 mm. (30% yield).

EXAMPLE 16

Methyl 3-methyl-5,6,7,8-tetrahydroquinoline-8-carboxylate

The title compound was prepared from 3-methyl-5,6,7,8-tetrahydroquinoline according to the general method described in Example 1B and isolated as a pale yellow oil b.p. 120°/0.25 mm. (80% yield). The hydrochloride was prepared in the usual way (cf Example 6B) and isolated as colourless needles from ethanol/ether m.p. 146° (Found: C, 59.9; H, 6.7; N, 6.0. $C_{12}H_{15}NO_2HCl$ requires: C, 59.60; H, 6.7; N, 5.8%).

EXAMPLE 17

3-Methyl-5,6,7,8-tetrahydroquinoline-8-carboxamide

The title compound was prepared from methyl 3-methyl-5,6,7,8-tetrahydroquinoline-8-carboxylate by the method described in Example 2 and was isolated as colourless needles from hexane m.p. 118° (50% yield) (Found: 69.60; H, 7.5; N, 14.8; $C_{11}H_{14}N_2O$ requires: C, 69.5; H, 7.4; N, 14.7%).

EXAMPLE 18

3-Methyl-5,6,7,8-tetrahydroquinoline-8-thiocarboxamide

3-Methyl-5,6,7,8-tetrahydroquinoline-8-carboxamide was treated with $P_2S_5$ to give 3-methyl-8-cyano-5,6,7,8-tetrahydroquinoline which was treated with $H_2S$ as described in Example 8 giving the title compound as colourless needles from benzene m.p. 151° (50% yield) (Found: C, 63.71; H, 6.85; N, 13.38% $C_{11}H_{14}N_2S$ requires: C, 64.04; H, 6.84; N, 13.58%).

The hydrochloride was prepared by dissolving the title compound in the minimum amount of isopropanol and then adding a solution of ether saturated with dry HCl gas. The hydrochloride precipitated as colourless needles m.p. 219° (Found: C, 54.33; H, 6.23; N, 11.42% $C_{11}H_{14}N_2SHCl$ requires: C, 54.42; H, 6.23; N, 11.54%).

EXAMPLE 19

Methyl-3-methyl-5,6,7,8-tetrahydroquinoline-8-carboxylate n-Butylbromide (285 ml.) in dry ether (500 ml.) was added to clean lithium wire (42 g., 6 m) in dry ether (1 l.) under nitrogen at such a rate to maintain an internal temperature of −15° C. Upon completion of the addition the reaction mixture was stirred until the temperature rose to 10° C (approx. 2 hours). The concentration of butyl lithium was calculated by standardising against N/10 HCl and the quantity of 3-methyl-5,6,7,8-tetrahydroquinoline required in the next stage adjusted to have a 1.2 m excess of butyl lithium.

A stirred solution of 3-methyl-5,6,7,8-tetrahydroquinoline 147 g., 1 m) in dry ether (700 ml.) was treated with a freshly prepared solution of butyl lithium (860 ml. of a 1.4 M solution i.e. 1.2 m) under nitrogen. The reaction mixture was stirred for an additional 15 min. and a slow stream of dry $CO_2$ gas bubbled into the reaction mixture until colourless. The reaction mixture was diluted with water (1.2 l), filtered and the aqueous phase separated and extracted with ether (3 × 500 ml.). The combined ethereal extracts were processed to give recovered 3-methyl-5,6,7,8-tetrahydroquinoline (40 g.) b.p. 116°-20°/15 mm.

The aqueous layer was evaporated to dryness and the residual solid treated with a solution of methanol previously saturated with dry HCl gas (1.5 l) and allowed to stand at room temperature for 12 hours. The volatiles were removed in vacuo. The residual oil was redissolved in water (1 l.), extracted with ether (3 × 250 ml.) and the extracts discarded. The aqueous solution was adjusted to pH 9.0 with $Na_2CO_3$ and extracted with ether (4 × 250 ml.). The combined extracts were dried and the solvent removed in vacuo to give the title compound as a pale yellow oil (85 g. 42%) GLC (10% SE30, T = 200°) $R_1$ = 3.25 min, 93% pure.

EXAMPLE 20

Methyl-3-methyl-5,6,7,8-tetrahydroquinoline-8-carboxylate

A solution of 3-methyl-5,6,7,8-tetrahydroquinoline (5 g., 0.034 m) in dry ether (50 ml.) was treated portionwise with a solution of butyl lithium in hexane (0.04 m) under nitrogen and the mixture allowed to stand at room temperature for 30 minutes. A slow stream of $CO_2$ gas was bubbled in until the reaction mixture was colourless. A further 0.02 m. of butyl lithium in hexane solution was added. The mixture was allowed to stand for 30 minutes and then treated with dry $CO_2$ gas as above. The reaction mixture was diluted with water (20 ml.), the aqueous layer extracted with ether (3 × 50 ml.) and the combined extracts retained for recovery of unreacted 3-methyl-5,6,7,8-tetrahydroquinoline. The aqueous phase was evaporated to dryness in vacuo. The resultant solid was treated with methanol previously saturated with dry HCl gas (50 ml.) and allowed to stand at room temperature for 3 hours. The solvent was removed and the residual oil dissolved in water (20 ml.) and extracted with ether (3 × 25 ml.) and the extracts discarded. The aqueous phase was adjusted to pH 9.0 with $Na_2CO_3$ and extracted into ether (3 × 50 ml.). The combined extracts were dried and evaporated in vacuo to give the title compound as a colourless oil (4.3 g., 60%) GLC (10% SE30, T = 200°). $R_1$ = 3.25 min. 98% pure.

EXAMPLE 21

3-Methyl-5,6,7,8-tetrahydroquinoline-8-carboxamide.

A mixture of methyl-3-methyl-5,6,7,8-tetrahydroquinoline-8-carboxylate (25 g., 0.13 m), formamide (11.6, 0.26 m) and sodium methoxide (from 2.99 g., 0.13m sodium) was heated with stirring in an oil bath at 120° for 1 hour. The reaction mixture was further heated at 100° for 3 hours under reduced pressure (15 mmHg). The cooled reaction mixture was diluted with 2N HCl to give an acidic solution which was extracted with ethylacetate (2 × 50 ml.) and the combined extracts discarded. The aqueous solution was adjusted to pH 9.0 with solid $Na_2CO_3$, saturated with NaCl and extracted with chloroform (3 × 100 ml.). The combined extracts were dried and evaporated to give a pale yellow oil which solidified on trituration with n-hexane. Recrystallisation from ethylacetate gave the title compound as colourless cubes (18.6 g., 88%) m.p. 110°. Found: C, 69.6; H, 7.4; N, 14.4%. $C_{11}H_{14}N_2O$ requires: C, 69.5; H, 7.4; N, 14.7%.

EXAMPLE 22

3-Methyl-5,6,7,8-Tetrahydroquinoline-8-carboxamide

A mixture of methyl-3-methyl-5,6,7,8-tetrahydroquinoline-8-carboxylate (25 g. 0.13 m), formamide (11.6 g., 0.26 m) and sodium methoxide (from 2.99 g., 0.13 m sodium) was heated on a steam bath for 1 hour while bubbling nitrogen through the mixture, to blow off the methyl formate produced in the reaction. The cooled reaction mixture was diluted with 2N HCl and worked up as described in Example 21 to give the title compound in 90% yield.

EXAMPLE 23

3-Methyl-5,6,7,8-tetrahydroquinoline-8-thiocarboxamide

A solution of 3-methyl-5,6,7,8-tetrahydroquinoline-8-carboxamide (27.9 g. 0.14 m) in dry pyridine (300 ml.), saturated with $H_2S$ gas, was treated with $P_2S_5$ (26 g., 0.14 m) and heated at reflux for 45 min. whilst maintaining a slow stream of $H_2S$ gas. The reaction mixture was evaporated to dryness in vacuo and cooled to 0° C, made alkaline with 10% sodium hydroxide and the solution extracted with chloroform (3 × 100 ml.). The combined extracts were washed with brine, dried and evaporated in vacuo. The residual oil was triturated with benzene and the solid filtered and recrystallised from benzene to give the title compound as pale yellow needles m.p. 149° (21.8 g., 87%). The hydrochloride was prepared as already described in Example 18 and isolated as colourless needles m.p. 219° C.

EXAMPLE 24

Methyl 3-methyl-5,6,7,8-tetrahydroquinoline-8-carboxylate

Charge a 3-necked flask with 3-methyl-5,6,7,8-tetrahydroquinoline (45 g. 0.29 moles) and ether (400 ml.). Stir. Add phenyl lithium solution (330 ml. of a 1 molar solution 0.3 moles in ether) at a rate to give gentle reflux. Maintain reflux for 2 hours. Cool in an ice-bath and bubble $CO_2$ through solution till no further change. Add water (700 ml.) to dissolve solid. Separate and wash aqueous layer with ether (3 times). Evaporate aqueous layer to dryness in vacuo. To the residue add a saturated solution (1 liter) of methanolic HCl and stand overnight at room temperature. Evaporate to dryness and dissolve residue in water. Wash water with ether (3 times). Basify aqueous solution with solid sodium carbonate and extract with ether (a heavy white solid also precipitates, but this does not interfere with the extraction). Wash ether layer with water, then brine. Dry and evaporate. Yield 25 g. (44%). GLC = 88% pure.

EXAMPLE 25

Methyl-3-methyl-5,6,7,8-tetrahydroquinoline-8-carboxylate

A solution of 15% n-butyl lithium in hexane (51 ml. ca. 0.12 m) was added portionwise to a solution of 3-methyl-5,6,7,8-tetrahydroquinoline (14.7 g., 0.1 m) in ether (100 ml.) and the mixture allowed to stand at room temperature for 1 hour and then added dropwise to a cooled, stirred solution of methylchloroformate (9.45 g., 0.1 m) in ether (100 ml.). The mixture was stirred at 50° C for 1 hour. The reaction mixture was diluted with water (20 ml.) and then treated with 2N HCl until acidic. The ethereal solution was separted and washed with 2N HCl (2 × 25 ml.). The combined aqueus washings were extracted with ether and the ethereal extracts discarded. The aqueous solution was adjusted to pH 9.0 with $Na_2CO_3$ and extracted with chloroform (3 × 50 ml.) and the combined extracts dried and evaporated to give a pale yellow oil (16 g) which on GLC examination (3% SE30) showed a mixture of unreacted tetrahydroquinoline (45%), the title compound (23%) and the 8,8-dicarboxylic ester (20%). The mixture was treated with 10% sodium hydroxide (75 ml.). and heated at reflux with stirring for 4 hours, cooled and extracted with ether (3 × 50 ml.). The combined ethereal extracts were dried, evaporated and distilled to give unreacted 3-methyl-5,6,7,8-tetrahydroquinoline (7 g.) b.p. 116°/18 mm Hg. The basic solution was adjusted to pH 8.5–9.0 with concentrated HCl and evaporated to dryness and the residue treated with methanol previously saturated with dry HCl (50 ml.) and allowed to stand at room temperature for 5 hours. The solvent was removed and the residue dissolved in water (20 ml.) and extracted with ether (2 × 50 ml.). The aqueous solution was adjusted to pH 9.0 with $Na_2CO_3$ and extracted with chloroform (3 × 25 ml.) and the combined extracts dried and evaporated to give the title compound (3 gm.).

EXAMPLE 26

3-Methyl-5,6,7,8-tetrahydroquinoline-8-thiocarboxamide hydrochloride

Crystal Form A

3-Methyl-5,6,7,8-tetrahydroquinoline-8-thiocarboxamide (1 g.) prepared as described in Example 18 was dissolved in boiling isopropylalcohol (25 ml.), filtered and allowed to cool to 40° C. An excess of an ethereal solution of hydrogen chloride was added followed by sufficient ether to cause turbidity. On cooling the title compound was isolated as fine colourless needles (0.95 g.) mpt 244° C. Found: C, 54.3; H, 6.2; N, 11.4%. $C_{11}H_{14}N_2S.HCl$ requires C, 54.4; H, 6.2; N, 11.5%. I.R. $\gamma_{max}^{Nujol\ Mull}$ 3300 (shoulder), 3230 (broad), 3060 (broad), 2540 (broad), 1650 (strong), 1605, 1555 cm$^{-1}$. This I.R. Spectrum was identical with that exhibited by the product of Example 18.

Crystal Form B

3-Methyl-5,6,7,8-tetrahydroquinoline-8-thiocarboxamide (1 g.) prepared as described in Example 18 was dissolved in boiling isopropyl alcohol (15 ml.) and a slight excess of an ethereal solution of hydrogen chloride added without cooling. The title compound was obtained as fine colourless needles (950 mg) m.p. 244° C. Found: C, 54.58; H, 6.29; N, 11.34%. $C_{11}H_{14}N_2S.HCl$ requires C, 54.42; H, 6.23; N, 11.54%. I.R. $\nu_{max}^{Nujol\ mull}$ 3260 (broad), 3220 (broad), 3050, 2630 (broad), 1655–1630 (3 sharp bands), 155cm$^{-1}$.

Crystal Form B - Alternative Method

3-Methyl-5,6,7,8-tetrahydroquinoline-8-thiocarboxamide (0.5 g.) was dissolved in methanol (1 ml.) and treated with methanol saturated with hydrogen chloride (1 ml.) and the solution heated to boiling. Ethyl acetate was added, whilst the methanol evaporated, until turbid. On cooling the title compound was isolated as fine colourless needles (0.4 g.) m.p. 244°. Found: C, 54.11; H, 6.18; N, 11.31%. $C_{11}H_{14}N_2S.HCl$ requires: C, 54.42; H, 6.23; N, 11.54%. Crystal Form A could not be converted into crystal form B by crystallising from isopropylalcohol/ether or methanol/ethyl acetate.

Form A on standing for 2–3 days reverted to Form B. Form A could also be converted to Form B by heating at 40° C under vacuum for 6 hours.

EXAMPLE 27

3-Methyl-5,6,7,8-tetrahydroquinoline-8-carboxamide

Crystal Form A

3-Methyl-5,6,7,8-tetrahydroquinoline-8-carboxamide (1 g.) prepared as described in Example 17 was dissolved in boilng di-isopropyl ether (80 ml.), filtered and allowed to cool. The title compound was isolated as fine colourless cubes (0.85 g.), m.p. 118° C. Found: C, 69.6; H, 7.5; N, 14.8%. $C_{11}H_{14}N_2O$ requires C, 69.5; H, 7.4; N, 14.7%. I.R. $\nu_{max}^{nujol}$ 3395, 3195, 1650 (strong), 1620, 1605 (shoulder), 1595, 1560, 1235, 875 (strong), 620 (strong) cm$^{-1}$. The I.R. Spectrum was identical with that of the product of Example 17.

Crystal Form B

3-Methyl-5,6,7,8-tetrahydroquinoline-8-carboxamide (1 g.) prepared as described in Example 17 was dissolved in boilng ethyl acetate (2 ml.), filtered and allowed to cool. The title compound was isolated as colourless rhombic crystals (0.80 g.) m.p. 113°. Found: C, 68.81; H, 7.40; N, 14.45%. $C_{11}H_{14}N_2O$ requires C, 69.50; H, 7.40; N, 14.70%. I.R.$\nu_{max}^{nujol}$ 3395, 3280, 3185, 1680 (strong) 1605, 1595, 1560, 900 (strong), 575 (strong) cm$^{-1}$.

The crystal forms A and B can be interconverted by crystallisation from the appropriate solvents. Thus crystallisation of form A from ethyl acetate will give form B and crystallisation of form B from di-isopropyl ether will give form A.

EXAMPLE 28

3-Methyl-5,6,7,8-tetrahydroquinoline-8-(N-methyl)thiocarboxamide

Methyl-3-methyl-5,6,7,8-tetrahydroquinoline-8-carboxylate (5 gm.) was dissolved in 33% methylamine in ethanol (50 ml.) and the solution heated at 150° for 24 hours in a stainless steel bomb. The solvent was removed in vacuo and the residual oil crystallised on standing. Recrystallization from 2-propanol/n-hexane gave 3-methyl-5,6,7,8-tetrahydroquinoline-8-(N-methyl)carboxamide as colourless needles (4 gm., 85%. A sample was characterised as the hydrochloride which was obtained by treating a solution of the base in ethanol with ethereal HCl and isolated as colourless needles m.p. 185°. (Found: C, 59.81; H, 7.11; N, 11.34%. $C_{12}H_{16}N_2O.HCl$ requires C, 59.87; H, 7.12; N, 11.64.

A solution of 3-methyl-5,6,7,8-tetrahydroquinoline-8-(N-methyl)carboxamide (1.2 g.) in pyridine (9 ml.) was treated with phosphoric pentasulphide (1.2 g.) and the mixture heated at reflux for 3 hours. The solvent was removed in vacuo and the residue treated with a 10% aqueous solution of sodium hydroxide until alkaline. The solution was extracted with chloroform (3 × 50 ml.) and the combined extracts washed with water (2 × 20 ml.) brine, dried and evaporated. The residual oily solid was recrystallised from benzene to give the title compound as colourless needles (0.9 g., 65%) m.p. 159° (Found: C, 65.12; H, 7.26; N, 12.56% $C_{12}H_{16}N_2S$ requires: C, 64.41; H, 7.32; N, 12.72%).

EXAMPLE 29

3-Methyl-5,6,7,8-tetrahydroquinoline-8-(N-n-butyl)-thiocarboxamide

Following the general procedure of Example 28, methyl-3-methyl-5,6,7,8-tetrahydroquinoline-8-carboxylate is treated with n-butylamine to give 3-methyl-5,6,7,8-tetrahydroquinoline-8-(N-n-butyl)carboxamide which is treated with phosphorus pentasulphide in pyridine to give the title compound which is obtained as a yellow oil. The oil is dissolved in an excess of ether saturated with HCL gas. The resulting solid is recrystalized from isopropanol to give the hydrochloride of the title compound as colourless needles m.p. 195° D(dec.)

EXAMPLE 30

Sym. Octahydrocridine-4-thiocarboxamide

Sym. octahydroacridine was prepared by converting cyclohexanone to di-(2-oxo-cyclohex-1-yl)-methane and further reacting with hydroxylamine according to the method of Gill et al. (JACS 1952, 74, 4923) and was isolated as a colourless oil b.p. 110°–15°/0.5 mm. in 40% overall yield.

A solution of sym. octahydroacridine (5 gm. 0.026 m.) in dry ether (50 ml.) was treated dropwise with a 15% solution of butyl lithium in hexane (11 ml. 0.026 m) and the mixture stirred at room temperature for 15 min. under an atmosphere of nitrogen. The nitrogen was replaced by $CO_2$ gas which was bubbled through the reaction mixture until colourless. The reaction mixture was diluted with water (50 ml.) and the organic layer separated and the aqueous phase extracted with ether (2 × 50 ml.). The combined extracts were retained for recovery of sym. octahydroacridine. The aqueous phase was evaporated to dryness, the residue treated with methanol previously saturated with dry HCl (50 ml.) and the solution allowed to stand at room temperature for 3 hours. The solvent was removed in vacuo the residue diluted with water (20 ml.) and extracted with ether. The aqueous phase was adjusted to pH 10. with solid $Na_2CO_3$ and extracted with ether (3 × 20 ml.). The combined extracts were washed with brine, dried and evaporated to give methyl-sym. octahydroacridine-4-carboxylate. (1 gm. 15%).

A solution of methyl-sym octahydroacridine-4-carboxylate (5 gm) in methanol previously saturated with ammonia (80 ml.) was heated at 140° for 3 days in a stainless steel bomb. The solvent was removed and the residual solid recrystallised from di-isopropyl ether to give sym. octahydroacridine-4-carboxamide as colourless needles (2.6 g, 57%) m.p. 159° (Found: C, 72.98; H, 8.04; N, 12.01%. $C_{14}H_{18}N_2O$: requires: C, 73.01; H, 7.88; N, 12.17%).

A solution of sym. octahydroacridine-4-carboxamide (1.8 gm.) in pyridine (17 ml.) was treated with hydrogen sulphide for 5 mins. The reaction mixture was treated with phosphorus pentasulphide (1.4 g.) and heated at reflux for 45 mins maintaining a slow stream of hydrogen sulphide throughout. The cooled reaction mixture was evaporated and the residue treated with 10% sodium hydroxide until alkaline. The aqueous solution was extracted with chloroform (3 × 50 ml.) and the combined extracts washed with brine, dried and evaporated and the residual solid recrystallised from di-isopropyl ether giving the title compound as a pale yellow powder (0.3 g. 16%) m.p. 104°–6° (solidifies and remelts at 148°). (Found: C, 68.69; H, 7.54; 10.98%. $C_{14}H_{18}N_2S$ requires: C, 68.26; H, 7.36; N, 11.37%).

EXAMPLE 31

3-Methyl-5,6,7,8-tetrahydroquinoline-8-thiocarboxamide oxalate

To a solution of 3-methyl-5,6,7,8-tetrahydroquinoline-8-thiocarboxamide (1 g.) in hot ethanol (10 ml.) was added a solution of oxalic acid dihydrate (650 mg.) in hot ethanol (6.5 ml.). The solution was filtered and allowed to cool when the oxalate crystallised. The oxalate was removed by filtration, washed with ether and dried. Yield 1 g. m.p. 186°–8° C. Found: C, 52.71%; H, 5.63%; N, 9.19%. Calc. for $C_{13}H_{16}N_2O_4S$: C, 52.70%; H, 5.44%; N, 9.46%.

EXAMPLE 32

3-Methyl-5,6,7,8-tetrahydroquinoline-8-thiocarboxamide tartrate

To a solution of 3-methyl-5,6,7,8-tetrahydroquinoline-8-thiocarboxamide (13 g.) in hot isopropylalcohol (130 ml.) was added a solution of 9.5 g. tartaric acid in hot isopropylalcohol (65 ml.). The solution was filtered and allowed to cool. The precipitated crystals of the tartrate were removed by filtration, washed with a little cold isopropyl alcohol and dried. Yield 10.2g.m.p.158°–160° C. Found: C,50.56% H, 5.67%; N, 7.90%. Calc. for $C_{15}H_{20}N_2O_6S$ : C, 50.55%; H, 5.65%; N, 7.86%.

EXAMPLE 33

3-Methyl-5,6,7,8-tetrahydroquinoline-8-thiocarboxyamide

3-Methyl-8-cyano-5,6,7,8-tetrahydroquinoline (1.7 g., 0.01 m.) and thioacetamide (1.5 g., 0.02 m.) were dissolved in dimethylformamide (50 ml.), and the solution saturated with dry hydrogen chloride gas and then heated on a steam bath for 4 hours. The cooled reaction mixture was poured onto water (200 ml.), washed with ethyl acetate (2 × ml) and the extracts discarded. The aqueous solution was adjusted to pH 10.0 with 46% sodium hydroxide and extracted into methylene chloride (2 × 200 ml.). The combined extracts were dried (sodium sulphate), evaporated i vacuo and the residual oil triturated with isopropanol and filtered. Recrystallization from benzene gave the title compound as pale yellow needles (1.3 g., 63%) m.p. 149°.

EXAMPLE 34

Methyl-3-methylcyclohepteno[b]pyridine-9-carboxylate

3-Methylcyclohepteno[b]pyridine was prepared from cycloheptanone and 3-amino-2-methyl-acrolein according to the method of Breitmaier (Tet. Lett 1970, 38, 3291) and in the manner described in the synthesis of 5,6,7,8-tetrahydroquinoline (Example 11) and was isolated as a colourless oil b.p. 140° /14 mm.

A solution of 15% n-butyl lithium in hexane (16 ml. ca. 0.04 m) was added portionwise to a solution of 3-methylcyclohepteno[b]pyridine (5 g. 0.03 m) in ether (50 ml.) under nitrogen and the mixture allowed to stand at room temperature for 30 minutes. The mixture was treated with $CO_2$ gas until the red colour was discharged and the solvent was removed in vacuo. The residue was dissolved in water (25 ml.) and extracted with ether (3 × 50 ml.). The aqueous solution was evaporated in vacuo and the residue treated with methanol previously saturated with HCl gas (100 ml.) and allowed to stand at room temperature for 12 hours. The solvent was removed and the residual oil was dissolved in water (50 ml.) and extracted with ether (3 × 50 ml.). The aqueous solution was adjusted to pH 9.0 with sodium carbonate and extracted into ether (3 × 50 ml.). The combined extracts were dried, evaporated in vacuo to give the title compound as a pale yellow oil (0.8 g., 11%) GLC : $R_T$ = 6.1/4 min. (F11, 10% SE30, T = 150°). I.R. Spectrum: $v_{max}^{film}$ 1740; 1460; 1440, 1120–1200 (broad) cm$^{-1}$.

EXAMPLE 35

Methyl-3-methylcyclopenteno[b]pyridine-7-carboxylate

3-Methylcyclopenteno[b]pyridine was prepared from cyclopentanone and 3-amino-2-methylacrolein according to the method of Breitamaier (Tet. Lett. 1970, 38, 3291) and was isolated as a colourless oil b.p. 100°–105°/15 mm.

A solution of 3-methylcyclopenteno[b]pyridine (10 g. 0.078 m.) in ether (150 ml.) was treated with a 15% solution of n-butyl lithium in hexane (30 ml. ca. 0.08 m) and the mixture treated with $CO_2$ gas. The lithium salt of 3-methylcyclopenteno[b]pyridine-8-carboxylic acid was isolated and esterified with methanol previously saturated with HCl gas as described for methyl-3-methylcyclohepteno[b]pyridine-9-carboxylate (Example 34). The title compound was isolated as a pale yellow oil (1.1 g., 10%) GLC $R_T$ = 1.1/2 min. (Pye 104, 3% SE30, T = 200°). I.R. Spectrum $v_{max}^{Film}$ 1738, 1460, 1422, 1160–1220 (broad) cm$^{-1}$.

EXAMPLE 36

Methyl-3,7,7-trimethyl-5,6,7,8-tetrahydroquinoline-8-carboxylate 3,7,7-Trimethyl-5,6,7,8-tetrahydroquinoline (17.5 g., 0.1 m) was dissolved in dry ether (200 ml.) and treated with a solution of n-butyl lithium in hexane (15% solution, 56 ml.) under nitrogen. The reaction mixture was allowed to stand at room temperature for 30 minutes and then treated with $CO_2$ gas until the intense red colour was discharged. The solvent was removed and the residual oily solid dissolved in water (20 ml.) then extracted with ether (3 × 50 ml.). The ethereal extracts were retained to recover unreacted starting material. The aqueous solution was evaporated to dryness, the residue treated with methanol previously saturated with dry HCl (100 ml.) and the solution allowed to stand at room temperature for 8 hours. The solvent was removed and the residual oil dissolved in water (50 ml) and extracted with ether (3 × 50 ml.) and the extracts discarded. The aqueous solution was adjusted to pH 9.0 with sodium carbonate and extracted with ether (3 × 50 ml.). The combined extracts were dried and evaporated in vacuo to give the title compound as a pale yellow oil (1.8 g., 10% I.R. Spectrum $v_{max}^{film}$ 1748, 1570, 1460, 1160, 1030 cm$^{-1}$. GLC : $R_T$ = 3.1/2 min. (F11, 2% OV17, T = 150°).

The picrate of the title compound was formed by dissolving the free base (100 mg) in ethanol (1 ml.) and adding a saturated solution of picric acid in ethanol (5 ml.) and allowing the picrate to crystallise. The picrate was removed by filtration, dissolved in the minimum volume of ethanol and precipitated by adding ether giving yellow needles m.p. 95°–7°.

Analysis Found: C, 50.2; H, 4.7; N, 12.1% $C_{14}H_{19}NO_2$ picrate ¾ $H_2O$ Requires: C,50.5; H, 5.0; N, 11.8%

EXAMPLE 37

3-Methyl-5,6,7,8-tetrahydroquinoline-8-thiocarboxamide

To a solution of 3-methyl,5,6,7,8-tetrahydroquinoline (10 g; 0.068 m.) in dry hexane (50 ml.) was added 50 ml. of a 15% solution of n-butyl lithium in hexane (0.09 m.) dropwise with stirring under an atmosphere of nitrogen. The dark red solution was stirred for 15 minutes at room temperature and then treated with carbon disulphide (10 ml.) The resulting pale yellow suspension was poured with water (100 ml.) and the aqueous solution was washed with ether (3 × 10 ml.).

The aqueous solution of the lithium salt of 3-methyl-5,6,7,8-tetrahydroquinoline-8-dithiocarboxylic acid was stirred vigorously and methyl iodide (40 ml.) added. The solution was stired at room temperature for 2½ hours and extracted with ether (3 × 75 ml.). The ether solution was dried over anhydrous magnesium sulphate and evaporated. Methyl 3-methyl-5,6,7,8-tetrahydroquinoline-8-dithiocarboxylate was left as a red oil.

The oil was dissolved in methanol previously saturated with ammonia (200 ml.) and the solution allowed to stand for 16 hours. The solvent was evaporated and the residue dissolved in ether (100 ml.). The ethereal solution was washed with water and the aqueous layer discarded. The solution was then extracted with 2N HCl (50 ml.) and water (50 ml.). The combined extracts were washed with ether and the pH of the solution adjusted to 9 with saturated sodium carbonate solution. The solution was extracted with ether (3 × 50 ml.) and the ethereal solution dried over, anhydrous magnesium sulphate and evaporated to give the crude 3-methyl-5,6,7,8-tetrahydroquinoline-8-thiocarboxamide (2.5 g.) tlc. on Silica gel F254 in ethyl acetate: $R_f$=0.4 and in ethanol $R_f$=0.8 identical with authentic material.

EXAMPLE 38

8-Cyano-5,6,7,8-tetrahydroquinoline 5,6,7,8-Tetrahydroquinoline-8-carboxamide (2 g.) was refluxed and stirred with $P_2S_5$ (1.4 g.) in pyridine 25 ml. for three hours. The mixture was evaporated to dryness in vacuo and then dilute sodium hydroxide was added to the residue followed by solid potassium carbonate. The product was extracted into chloroform and the chloroform extract washed with water and dried over MgSO$_4$. The dried extract was evaporated to dryness and the residue purified using column chromatography on silica gel with benzene/ethyl acetate (4:1) as eluent. The nitrile was dissolved in ethanol/ether and ethereal HCl added. The solution was evaporated to dryness giving the hydrochloride of the title compound as the quarter hydrate 800 mg. m.p. 185° dec.

Analysis Found: C,60.8; H, 5.7; N, 14.0% C$_{10}$H$_{10}$N$_2$HCl ¼ H$_2$O requires C,60.5; H, 5.8; N, 14.10%

EXAMPLE 39

3-Methyl-5,6,7,8-Tetrahydroquinoline-8-carboxylic acid

Methyl-5,6,7,8-tetrahydroquiniline-8-carboxylate (5 g.) was treated with 10% NaOH (40 ml.) and heated under reflux for 1½ hours. The cooled reaction mixture was extracted with ether and the aqueous layer was acidified to pH7 with acetic acid filtered and evaporated to dryness under reduced pressure. The residue was triturated with benzene. The benzene solution was filtered and evaporated under reduced pressure and the residues were triturated with ether giving the sodium salt of the title compound as a white powder 1.8 g. Found C,60.0; H, 5.6; N,6.4% C$_{11}$H$_{12}$NO$_2$N$_1$ ½ H$_2$O requires C,59.6; H,5.8; N, 6.4% pKa 3.42, and 6.72 were recorded.

A further 1.4 g. of the sodium salt was obtained by further extraction of the benzene insoluble material.

EXAMPLE 40

8-Cyano-3-Methyl-5,6,7,8-tetrahydroquinoline

3-Methyl-5,6,7,8-tetrahydroquinoline-8-carboxamide (3.6 g.) in pyridine (54 ml.) was treated with P$_2$S$_5$ (7.56 g.) and the mixture heated at reflux with stirring for 3 hours. The solvent was removed under reduced pressure and the residue cooled in ice-water then made basic with 10% NaOH. The basic solution was extracted with chloroform (3 times) and the combined extracts extracted with 2NHCl (twice). The combined acid extracts were basified with solid sodium carbonate and extracted into chloroform (3 times). The combined chloroform extracts were washed with brine dried (MgSO$_4$) and evaporated to give the title compound 1.7 g. This was converted to the hydrochloride by dissolving in ether and adding ethereal HCl. An oily residue was formed from which the supernatent liquid was decanted. The residue was triturated twice with dry ether and the remaining solid recrystallised from isopropyl alcohol giving the hydrochloride of the title compound m.p. 189° C.

Analysis Found: C, 63.08; H, 6.26; N, 13.34% C$_{11}$H$_{12}$N$_2$HCl requires: C, 63.30; H, 6.28; N, 13.4%

EXAMPLE 41

2-Phenyl-4(4'-methoxyphenyl)-5,6,7,8-tetrahydroquinoline-8-thiocarboxamide

A hot solution of sodium hydroxide [(15 g.in water (15 ml.)] is added to a solution of 1-phenyl-3-(4'-methoxyphenyl)prop-2-enone (10.7 g. 0.045 mol.) and cyclohexanone (20 g. 0.2 mol.) in ethanol (150 ml.) at 40° C and the mixture stirred at room temperature for 12 hours. The reaction mixture is diluted with water (200 ml.) and the resultant solid filtered, dried and recrystallised from ethanol to give 2-[(β-benzoyl-α-(4'-methoxyphenylethyl)]cyclohexanone as colorless needles m.p. 148° C (Found: C, 79.0, H, 7.4 C$_{22}$H$_{24}$O$_3$ requires: C, 78.5; H, 7.2%).

A solution of 2-[β-benzoyl-α-(4'-methoxyphenylethyl)]cyclohexanone (7.6 0.021 mol.) in ethanol (25 ml.) is treated with hydroxylamine hydrochloride (3.42 g., 0.05 mol.) and the mixture heated at reflux with stirring for 2 hours. The cooled reaction mixture is diluted with water (50 ml.) and the pH adjusted to 1.0 with conc.HCl and extracted with ether (2 × 50 ml.) and the extracts discarded. The aqueous solution is adjusted to pH 9.0 with Na$_2$CO$_3$ and extracted with ether (2 × 50 ml.) and the combined extracts washed with brine, dried (MgSO$_4$) and evaporated to give 2-phenyl-4(4'-methoxyphenyl)-5,6,7,8-tetrahydroquinoline as a colorless oil (5.8 g.) which is converted into methyl-2-phenyl-4(4'-methoxyphenyl)-5,6,7,8-tetrahydroquinoline-8-carboxylate following the method described in Example 19. The ester is converted into 2-phenyl-4(4'-methoxyphenyl)-5,6,7,8-tetrahydroquinoline-8-carboxamide following the method described in Example 22. The amide is converted into the title compound following the method described in Example 23.

EXAMPLE 42

3,8-Dimethyl-5,6,7,8-tetrahydroquinoline-8-thiocarboxamide 3,8-dimethyl-8-cyano-5,6,7,8-tetrahydroquinoline is treated with H$_2$S in pyridine in the presence of triethylamine following the general procedure of Example 5 and the title compound is isolated and recrystallised from benzene as the quarter hydrate, colorless meedles m.p. 164° C. This was converted to the hydrochloride by treatment in isopropanol with a solution of dry HCl gas in ether. The title compound hydrochloride crystallised as colorless needles m.p. 277° C.

EXAMPLE 43

4-Methyl-5,6,7,8-tetrahydroquinoline-8-thiocarboxamide

Following the general procedures of Example 19 22 and 23 4-methyl-5,6,7,8-tetrahydroquinoline is converted to the title compound, which is obtained as the hydrochloride, colorless needles m.p. 213° C.

EXAMPLE 44

3,7,7-Trimethyl-5,6,7,8-tetrahydroquinoline-thiocarboxamide

Methyl-3,7,7-trimethyl-5,6,7,8-tetrahydroquinoline-8-carboxylate obtained as described in Example 36 is converted to the 8-carboxamide following the general procedure of Example 22. The product is treated with phosphorus pentasulphide and H$_2$S in pyridine following the general procedure of Example 23 to give the title compound which is converted to the hydrochloride. The hydrochloride of the title compound is recrystallised from isopropanol as a 1.¼ hydrate m.p. 162° C.

EXAMPLE 45

1,2,3,5,6,7-Hexahydro-dicyclopenta[b,e]pyridine-3-thiocarboxamide hydrochloride A mixture of 2-(dimethylaminomethyl)cyclopentanone (87 g.) and cyclopentanone (210 g.) was heated at reflux for 12 hours. The excess cyclopentanone was removed by distillation and the residue was dissolved in ethanol (300 ml.) and treated with hydroxylamine hydrochloride (100 g.) and the mixture heated at reflux for 1½ hours. The cooled reaction mixture was dissolved in water (1 liter), washed with ether (3 × 200 ml.) and the aqueous phase adjusted to pH 10.0 with sodium carbonate and extracted with ether (3 × 200 ml.) the combined extracts were dried (MgSO$_4$) and the solvent removed to give a residual oil which was distilled at 0.2 mm to give 1,2,3,5,6,7-hexahydrodicyclopenta [b,e]pyridine as a colorless oil (50 g.) b.p. 100° C. The pyridine is converted to the methyl 3-carboxylate following the method described in Example 19 and the carboxylate converted to 1,2,3,5,6,7-hexahydro-dicyclopenta[b,e]-pyridine-3-carboxamide, by the general method described in Example 17. The carboxamide is isolated as colorless needles from methanol m.p. 188° C. (Found: C,71.1; H, 7.2; N, 14.3. C$_{12}$H$_{14}$N$_2$O requires: C, 71.3; H, 7.0; N, 13.9%).

The carboxamide (1.9 g.) is converted to the thioamide by the method described in Example 23 and isolated as a pale yellow solid which is converted to the hydrochloride by treating a solution of the base (600 mg.) in methanol (5 ml.) with excess ethereal hydrogen chloride. The resultant solid is recrystallized from methanol-ether to give the title compound as colorless needles m.p. 299° C. (Found: C,56.4; H,6.1; N, 10.8. C$_{12}$H$_{14}$N$_2$S.HCl requires: C,56.6; H, 5.9; N, 11.0%).

EXAMPLE 46

1,2,3,4,5,7,8,9,10,11-Decahydro-dicyclohepta[b,e]pyridine-5-thiocarboxamide hydrochloride A mixture of cycloheptanone (190 g.) and 2-(dimethylaminoethyl)-cycloheptanone (72.g) is heated at 170° C for 12 hours. The excess cycloheptanone is removed and the residue dissolved in ethanol (300 ml.), treated with hydroxylamine hydrochloride (100 g.) and the mixture heated at reflux for 2 hours, cooled, diluted with water (1 liter) and extracted with ether (2 × 300 ml.). The aqueous phase is adjusted to pH 10 with sodium carbonate and extracted with ether (3 × 250 ml.) and the combined extracts dried (MgSO$_4$) and the solvent removed to give a residual oil which is distilled at 0.2 mm to give 1,2,3,4,5,7,8,9,10,11-decahydro-dicyclohepta[b,e]pyridine (30 g.) b.p. 120° C. which is converted to the methyl-5-carboxylate by the general method described in Example 19. The carboxylate is treated with methanol saturated with ammonia to obtain 1,2,3,4,5,7,8,9,10,11-decahydro-dicyclohepta[b,e]-pyridine-5-carboxamide as colorless needles (1.5 g.) m.p. 179° C (Found: C, 74.5; H, 8.7; N, 10.7 Chd 16H$_{22}$N$_2$O requires: C, 74.4; H, 8.6; N, 10.9%). The amide (1.3 g.) is converted to the thioamide by the general method described in Example 23. The product is recrystallised from isopropanol to give the title compound as the hemi-hydrate m.p. 80° C (Found: C, 60.2; H, 7.5; N, 8.3. C$_{16}$H$_{22}$N$_2$S.HCl. ½H$_2$O requires C, 60.1; H, 7.6; N, 8.7%).

EXAMPLE 47

3-Methyl-cyclopenteno[b]pyridine-7-thiocarboxamide

The methyl carboxylate product of Example 35 is treated with methanol saturated with ammonia gas as described in Example 17 to obtain 3-methyl-cyclopenteo[b]pyridine-7-carboxamide m.p. 159° C. This is converted to the title compound hydrochloride (m.p. 198°-202° C) by the general method of Example 23.

EXAMPLE 48

5,6,7,8-Tetrahydro-2,3-dihydro-1H-cyclopenta[b]-quinoline-5-thiocarboxamide 2-(oxo-cyclopentyl)methyl cyclohexanone is prepared from 2-(dimethylaminomethyl)-cyclohexanone and cyclopentanone according to the method described in Ann. Chim., 1963, 53 (6), 819 and is isolated as a colorless oil in 80% yield b.p. 92°/0.05 mm. 5,6,7,8-Tetrahydro-2,3-dihydro-1H-cyclopenta[b]quinoline is prepared from 2-(2-oxocyclopentyl)methylcyclohexanone according to the method described in Ann.Chim., 1963, 53, (6), 819 and is isolated in 65% yield as a colorless oil b.p. 80°/0.05 mm. The hydrochloride is prepared for characterisation by treating an ethereal solution of the base with ethereal HCl and is isolated as the hemihydrate as colorless needles from ethanol-ether m.p. 104° C (Found: C, 65.7; H, 7.8; N, 6.6. C$_{12}$H$_{16}$N.HCl.½H$_2$O requires: C, 65.8; H, 7.8; N, 6 4%. 5,6,7,8-Tetrahydro-2,3-dihydro-1H-cyclopenta[b]-quinoline is converted to methyl 5,6,7,8-tetrahydro-2,3-dihydro-1H-cyclopenta[b]quinoline-5-carboxylate following the method described in Example 19 and this is converted to 5,6,7,8-tetrahydro-2,3-dihydro-1H-cyclopenta[b]-quinoline-5-carboxamide following the method described in Example 22. The amide is converted to the title compound, following the procedure of Example 23, and is recrystallised from isopropanol, dissolved in ether and treated with an excess of ethereal HCl. The resultant solid is recrystallised from ethanol-ether to give the hydrochloride of the title compound as the monohydrate m.p. 118° C. (Found: C, 54.6; H, 6.3; N, 10.0. C$_{13}$H$_{16}$N$_2$S.HCl H$_2$O requires: C, 54.4; H, 6.6; N, 9.8%)

EXAMPLE 49

3-Trifluoromethyl-5,6,7,8-Tetrahydroquinoline-8-thiocarboxamide

3-Trifluoromethyl-5,6,7,8-tetrahydroquinoline (1 mol) is converted to methyl 3-trifluoromethyl-5,6,7,8-tetrahydroquinoline-8-carboxylate by treatment with 1.2 mol n-butyl lithium (prepared from n-butyl-bromide and lithium wire) in dry ether under nitrogen,the reaction mixture being stirred for 15 min. when a slow stream of dry CO$_2$ gas is bubbled into the reaction mixture until colorless. The reaction mixture is diluted with water, filtered, and the aqueous phase separated and extracted with ether. The aqueous layer is evaporated to dryness and the residual solid lithium 3-trifluoromethyl-5,6,7,8-tetrahydroquinoline-8-carboxylate is treated with a solution of methanol previously saturated with dry HCl gas and allowed to stand for 12 hours at room temperature. The volatiles are removed in vacuo and the residual oil is redissolved in water and extracted with ether. The aqueous phase is adjusted to pH9 with sodium carbonate and extracted with ether (4 times). The combined ether extracts are dried and the solvent evaporated in vacuo to leave methyl 3-trifluoromethyl-5,6,7,8-tetrahydroquinoline-8-carboxylate.

The carboxylate (1 mol) is heated with formamide (2 mols) and sodium methoxide (1 mol) on a steam bath for 1 hour while bubbling nitrogen through the mixture to blow off methyl formate produced in the reaction. The cooled reaction mixture is diluted with 2NHCl to give an acidic solution which is extracted with ethylacetate.

The aqueous phase is adjusted to pH 9 with solid sodium carbonate, saturated with sodium chloride and extracted with chloroform (3 times). The chloroform extracts are dried and evaporated to leave 3-trifluoromethyl-5,6,7,8-tetrahydroquinoline-8-carboxamide which is recrystallised from ethyl acetate.

The amide (1 mol) is dissolved in dry pyridine saturated with $H_2S$ gas and treated with $P_2S_5$(1 mol) then heated at reflux for 45 min. while maintaining a slow stream of $H_2S$ gas. The reaction mixture is evaporated to dryness in vacuo and cooled to 0° C, made alkaline with 10% sodium hydroxide and the solution extracted with chloroform (3 times). The combined extracts are washed with brine, dried and evaporated in vacuo to give the title compound.

EXAMPLE 50

3-Phenyl-5,6,7,8-tetrahydroquinoline-8-thiocarboxamide 3-phenyl-5,6,7,8-tetrahydroquinoline is converted into methyl-3-phenyl-5,6,7,8-tetrahydroquinoline-8-carboxylate following the procedure described in Example 19. The ester is converted into 3-phenyl-5,6,7,8-tetrahydroquinoline-8-carboxamide by the method described in Example 22. The amide is converted into the title compound by the method described in Example 23.

Replacing 3-phenyl-5,6,7,8-tetrahydroquinoline by each of the following starting materials in the above-mentioned procedure the following compounds are prepared:

| Starting material | End Product |
| --- | --- |
| 3-p-tolyl-5,6,7,8-tetrahydroquinoline | 3-p-tolyl-5,6,7,8-tetrahydroquinoline-8-thiocarboxamide |
| 3-o-chlorophenyl-5,6,7,8-tetrahydroquinoline | 3-o-chlorophenyl-5,6,7,8-tetrahydroquinoline-8-thiocarboxamide |
| 3-p-nitrophenyl-5,6,7,8-tetrahydroquinoline | 3-p-nitrophenyl-5,6,7,8-tetrahydroquinoline-8-thiocarboxamide |
| 3-p-trifluoromethylphenyl-5,6,7,8-tetrahydroquinoline | 3-p-trifluoromethylphenyl-5,6,7,8-tetrahydroquinoline-8-thiocarboxamide |
| 3-p-methoxyphenyl-5,6,7,8-tetrahydroquinoline | 3-p-methoxy-phenyl-5,6,7,8-tetrahydroquinoline-8-thiocarboxamide |

EXAMPLE 51

3-Benzyl-5,6,7,8-tetrahydroquinoline-8-thiocarboxamide

3-Benzyl-5,6,7,8-tetrahydroquinoline is converted into methyl-3-benzyl-5,6,7,8-tetrahydroquinoline-8-carboxylate by the method described in Example 19. The ester is converted into 3-benzyl-5,6,7,8-tetrahydroquinoline-8-carboxamide by the method described in Example 22. The title compound is prepared from the amide by the method described in Example 23.

EXAMPLE 52

Following the procedure of Example 19 but substituting the indicated starting materials for 3-methyl-5,6,7,8-tetrahydroquinoline the indicated end products are obtained.

| 5,6,7,8-tetrahydroquinoline(THQ)derivative | |
| --- | --- |
| Starting Material | End Product |
| 4-trifluoromethyl-THQ | methyl-4-trifluoromethyl THQ-8-carboxylate |
| 3-n-butyl-THQ | methyl-3-n-butyl-THQ-8-carboxylate |
| 3-n-pentyl-THQ | methyl-3-n-pentyl-THQ-8-carboxylate |
| 2-phenethyl-THQ | methyl-2-phenethyl-THQ-8-carboxylate |
| 3-benzyl-THQ | methyl-3-benzyl-THQ-8-carboxylate |
| 3-phenpropyl-THQ | methyl-3-phenpropyl-THQ-8-carboxylate |
| 4-benzyl-THQ | methyl-4-benzyl-THQ-8-carboxylate |
| 4-phenpropyl-THQ | methyl-4-phenpropyl-THQ-8-carboxylate |
| 3,5-dimethyl-THQ | methyl-3,5-dimethyl-THQ-8-carboxylate |
| 3,6-dimethyl-THQ | methyl-3,6-dimethyl-THQ-8-carboxylate |
| 3,7-dimethyl-THQ | methyl-3,7-dimethyl-THQ-8-carboxylate |
| 3-methyl-5-n-butyl-THQ | methyl-3-methyl-5-n-butyl-THQ-8-carboxylate |
| 3-methyl-6-iso-propyl-THQ | methyl-3-methyl-6-iso-propyl-THQ-8-carboxylate |
| 4-n-hexyl-THQ | methyl-4-n-hexyl-THQ 8-carboxylate |
| 5-methyl-THQ | methyl-5-methyl-THQ-8-carboxylate |
| 6-ethyl-THQ | methyl-6-ethyl-THQ-8-carboxylate |
| 7-n-propyl-THQ | methyl-7-n-propyl-THQ-8-carboxylate |
| 5-phenethyl-THQ | methyl-5-phenethyl-THQ-8-carboxylate |
| 6-phenpropyl-THQ | methyl-6-phenpropyl-THQ-8-carboxylate |

EXAMPLE 53

Following the procedure of Example 22 but replacing methyl-3-methyl-5,6,7,8- -tetrahydroquinoline-8-carboxylate with each of the methyl ester products of Example 52 the following amides are obtained,

| 5,6,7,8-tetrahydroquinoline(THQ)derivative |
| --- |
| 4-trifluoromethyl-THQ-8-carboxamide |
| 3-n-butyl-THQ-8-carboxamide |
| 4-n-hexyl-THQ-8-carboxamide |
| 3-n-pentyl-THQ-8-carboxamide |
| 2-phenethyl-THQ-8-carboxamide |
| 3-benzyl-THQ-8-carboxamide |
| 3-phenpropyl-THQ-8-carboxamide |
| 4-benzyl-THQ-8-carboxamide |
| 4-phenpropyl-THQ-8-carboxamide |
| 3,5-dimethyl-THQ-8-carboxamide |
| 3,6-dimethyl-THQ-8-carboxamide |
| 3,7-dimethyl-THQ-8-carboxamide |
| 3-methyl-5-n-butyl-THQ-8-carboxamide |
| 3-methyl-6-isopropyl-THQ-8-carboxamide |
| 5-methyl-THQ-8-carboxamide |
| 6-ethyl-THQ-8-carboxamide |
| 7-n-propyl-THQ-8-carboxamide |
| 5-phenethyl-THQ-8-carboxamide |
| 6-phenpropyl-THQ-8-carboxamide |

EXAMPLE 54

Following the procedure of Example 23 but replacing 3-methyl-5,6,7,8-tetrahydroquinoline-8-carboxamide with each of the amide products of Example 53 the following thioamides are obtained:

| Substituent(s) | -5,6,7,8-tetrahydroquinoline-8-thiocarboxamide |
| --- | --- |
| 4-trifluoromethyl- | |
| 3-n-butyl- | |
| 4-n-hexyl- | |
| 3-n-pentyl- | |
| 2-phenethyl- | |
| 3-benzyl- | |
| 3-phenpropyl- | |
| 4-benzyl- | |
| 4-phenpropyl- | |
| 3,5-dimethyl- | |
| 3,6-dimethyl- | |
| 3,7-dimethyl- | |
| 3-methyl-5-n-butyl- | |

| Substituent(s) | -5,6,7,8-tetrahydroquinoline-8-thiocarboxamide |
|---|---|
| 3-methyl-6-isopropyl | |
| 5-methyl- | |
| 6-ethyl- | |
| 7-n-propyl- | |
| 5-phenethyl- | |
| 6-phenpropyl- | |

EXAMPLE 55

Following the procedure of Example 28 but substituting the following starting materials for the ester and amine respectively the following products are obtained:

| Starting Materials | | End Product |
|---|---|---|
| ester | amine | |
| methyl-2-phenyl-5,6,7,8-tetrahydroquinoline-8-carboxylate | ethylamine | 2-phenyl-5,6,7,8-tetrahydroquinoline-8-(N-ethyl)-thiocarboxamide |
| methyl-5,6,7,8-tetrahydroquinoline-8-carboxylate | methylamine | 5,6,7,8-tetrahydroquinoline-8(N-methyl)-thiocarboxamide |
| methyl-2-t-butyl-5,6,7,8-tetrahydroquinoline-8-carboxylate | ethylamine | 2-t-butyl-5,6,7,8-tetrahydroquinoline-8-(N-ethyl)thiocarboxamide. |
| methyl-2-methyl-5,6,7,8-tetrahydroquinoline-8-carboxylate | methylamine | 2-methyl-5,6,7,8-tetrahydroquinoline-(8-N-methyl)thiocarboxamide |
| methyl-4-methyl-5,6,7,8-tetrahydroquinoline-8-carboxylate | n-butylamine | 4-methyl-5,6,7,8-tetrahydroquinoline (8-N-n-butyl)-thiocarboxamide |
| methyl-3-methyl-cyclopenteno-[b]-pyridine-7-carboxylate | ethylamine | 3-methyl-cyclopenteno-[b]pyridine-7-(N-ethyl-thiocarboxamide |

EXAMPLE 56

Following the procedure of Example 47 but substituting the following starting materials the following end products are obtained:

| starting material | end product |
|---|---|
| methyl-2-methyl-cyclopenteno-[b]-pyridine-7-carboxylate | 2-methyl-cyclopenteno-[b]-pyridine-7-thio-carboxamide |
| methyl-4-methyl-cyclopenteno-[b]pyridine-7-carboxylate | 4-methyl-cyclopenteno-[b]-pyridine-7-thio-carboxamide. |
| methyl-5-methyl-cyclopenteno-[b]-pyridine-7-carboxylate | 5-methyl-cyclopenteno-[b]-pyridine-7-thio-carboxamide |
| methyl-3-phenyl-cyclopenteno-[b]-pyridine-7-carboxylate | 3-phenyl-cyclopenteno-[b]-pyridine-7-thio-carboxamide |
| methyl-4-phenethyl-cyclopenteno[b]-pyridine-7-carboxylate | 4-phenethyl-cyclopenteno-[b]-pyridine-7-thio-carboxamide |

EXAMPLE 57

Following the procedure of the indicated Examples but substituting other alcohols for methyl alcohol the following esters are prepared:

| Example | Alcohol | Ester obtained |
|---|---|---|
| 1B | ethanol | ethyl-2-phenyl-5,6,7,8-tetrahydroquinoline-8-carboxylate |
| 6B | t-butanol | t-butyl-5,6,7,8-tetrahydroquinoline-8-carboxylate |
| 9B | n-hexanol | n-hexyl-2-butyl-5,6,7,8-tetrahydroquinoline-8-carboxylate |
| 16 | n-butanol | n-butyl-3-methyl-5,6,7,8-tetrahydroquinoline-8-carboxylate |
| 19 | benzyl alcohol | benzyl-3-methyl-5,6,7,8-tetrahydroquinoline-8-carboxylate |
| 35 | t-butanol | t-butyl-3-methyl-cyclopenteno[b]pyridine-7-carboxylate |
| 36 | ethanol | ethyl-3,7,7-trimethyl-5,6,7,8-tetrahydroquinoline-8-carboxylate. |

EXAMPLE 58

The following further compounds may be prepared using procedures as descrbed above.

3,4-dimethyl-5,6,7,8-tetrahydroquinoline-8-thiocarboxamide mp 163°–5° C;

3,5-dimethyl-5,6,7,8-tetrahydroquinoline-8-thiocarboxamide as the hydrochloride mp 226° C;

3,6-dimethyl-5,6,7,8-tetrahydroquinoline-8-thiocarboxamide as the hydrochloride mp 237° C; and 2,4-dimethyl-5,6,7,8-tetrahydroquinoline-8-thiocarboxamide mp 84° C.

The following Examples illustrate pharmaceutical compositions in accordance with the invention.

| Example A | |
|---|---|
| Suspension | % w/v |
| Aluminium hydroxide gel B.P.5% Al$_2$O$_3$ | 80% = 4% Al$_2$O$_3$ |
| Magnesia Magma 12% w/v MgO | 10% |
| 5,6,7,8-tetrahydroquinoline-8-thiocarboxamide | 2.0% |
| Glycerin B.P. | 3.0% |
| Alcohol 60 O.P.* | 0.08% |
| Peppermint oil B.P. | 0.015% |
| Saccharin sodium B.P. | 0.01% |
| Methyl p-hydroxybenzoate sodium salt | 0.1% |
| Propyl p-hydroxybenzoate sodium salt | 0.02% |
| Butyl p-hydroxybenzoate sodium salt | 0.01% |
| Water q.s. ad | 100.00% |

*O.P. denotes overproof. 60 O.P. represents 91% w/v Ethanol/Water.

The above suspension is prepared by the following procedure. Add to the Alumina gel magnesia Magma followed by the 5,6,7,8-tetrahydroquinoline-8-thiocarboxamide dispersed in glycerin, the peppermint oil dissolved in alcohol, the saccharin sodium dissolved in water, and the p-hydroxybenzoates dissolved in water. Make up to volume with water and stir well. Dose: 5 ml. t.d.s.

| Example B | |
|---|---|
| Antacid Tablet (chewable) | |
| Saccharin | 1.0 mg. |
| Hydrated alumina sucrose powder | 750.0 mg. |
| 5,6,7,8-Tetrahydroquinoline-8-thio-carboxamide | 100.0 mg. |
| Mannitol B.P. | 170.0 mg. |
| Maize starch B.P. dried | 30.0 mg. |
| Talc.purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure.

Triturate peppermint oil with talc (screen 40 mesh). Add the triturate, and other ingredients to a blender and mix thoroughly.

Slug the powder to large hard slugs.

Granulate the slugs through a 14 mesh screen.

Compress the granules on a suitable compression machine to give tablets of the required size.

| Example C | |
|---|---|
| anti-ulcer tablet (without antacid) | mg/tablet |
| 5,6,7,8-Tetrahydroquinoline-8-thio-carboxamide | 100 mg. |
| Celutab | 147.5 mg. |
| Mag.Stearate | 2.5 mg. |
| | 250.0 mg. |

The tablets are prepared by the following method. Blend the ingredients in a suitable blender. Compress the blended ingredients on a suitable compression machine to form tablets of the above composition.

Celutab is a commercial product comprising 90-2% dextrose. 3-5% maltose remainder higher glucose saccharides. Spray crystallised.

EXAMPLE D

A suspension is prepared as descrbied in Example A but replacing 5,6,7,8-tetrahydroquinoline-8by 3-methyl-5,6,7,8-tetrahydroquinoline-8-thiocarboxamide.

EXAMPLE E

An antacid tablet is prepared as descrbied in Example B but replacing 5,6,7,8-tetrahydroquinoline-8-thiocarboxamide by 3-methyl-5,6,7,8-tetrahydroquinoline-8-thiocarboxamide.

EXAMPLE F

An anti-ulcer tablet is prepared as described in Example C but replacing 5,6,7,8-tetrahydroquinoline-8-thiocarboxamide by 3-methyl-5,6,7,8-tetrahydroquinoline-8-thiocarboxamide.

The invention includes a method of treating ulcers in an afflicted host which method comprises administering to said host a compound of formula I as defined above wherein X is $CSNHR^3$ and $R^3$ is as defined in connection with formula I.

We claim:

1. An anti-ulcer pharmaceutical composition comprising an effective amount of a compound of formula I

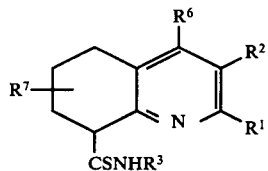

or an acid addition salt thereof with a pharmaceutically acceptable acid, wherein $R^1$, $R^2$ and $R^6$ are the same or different and are selected from hydrogen, trifluoromethyl, alkyl containing from 1 to 6 carbon atoms, phenylalkyl wherein the alkyl group has 1 – 6 carbon atoms, or phenyl groups or $R^1$ and $R^2$ taken together represent a polymethylene chain of 3 to 5 carbon atoms, $R^7$ represents hydrogen or from 1 to 3 groups selected from alkyl of 1 to 6 carbon atoms which may be substituted by alkoxy of 1 to 6 carbon atoms or trifluoromethyl, phenylalkyl wherein the alkyl group has 1 to 6 carbon atoms and phenyl groups, $R^3$ is hydrogen or alkyl of 1 to 6 carbon atoms, and any of the phenyl or the phenyl portion of any phenylalkyl groups $R^1$, $R^2$, $R^6$ and $R^7$ may be substituted by alkyl of 1 to 6 carbon atoms, lower alkoxy of 1 to 6 carbon atoms, halogen, nitro or trifluoromethyl with the provisos that (1) when $R^1$ and $R^2$ or $R^2$ and $R^6$ are both alkyl they are selected from normal and secondary alkyl groups and (2) when two alkyl $R^7$ groups are present on the same carbon atom then they are both n-alkyl groups and when two $R^7$ alkyl groups are present on adjacent carbon atoms they are selected from normal and secondary alkyl groups and a pharmaceutically acceptable carrier.

2. A pharmaceutical composition as claimed in claim 1, wherein the compound of formula I is one in which $R^1$, $R^2$, $R^6$ and $R^7$ are the same or different and are selected from hydrogen and lower alkyl of 1 to 4 carbon atoms, and $R^3$ is hydrogen or methyl.

3. A pharmaceutical composition as claimed in claim 1 wherein the compound of formula I is one in which $R^1$, $R^2$, $R^3$ and $R^6$ are selected from hydrogen and methyl.

4. A pharmaceutical composition as claimed in claim 1, wherein the compound of formula I is one in which $R^1$, $R^2$ and $R^6$ are selected from hydrogen and t-butyl and $R^3$ is hydrogen.

5. A pharmaceutical composition as claimed in claim 1 in which the compound of formula I is 3,4-dimethyl-5,6,7,8-tetrahydroquinoline-8-thiocarboxamide.

6. A pharmaceutical composition as claimed in claim 1 in which the compound of formula I is 2-methyl-5,6,7,8-tetrahydroquinoline-8-thiocarboxamide.

7. A pharmaceutical composition as claimed in claim 1 in which the compound of formula I is selected from 3-methyl-5,6,7,8-tetrahydroquinoline-8-thiocarboxamide and the pharmaceutically acceptable acid addition salts thereof.

8. A pharmaceutical composition as claimed in claim 1 in which the compound of formula I is 4-methyl-5,6,7,8-tetrahydroquinoline-8-thiocarboxamide.

9. A pharmaceutical composition as claimed in claim 1 in which the compound of formula I is 3-methyl-5,6,7,8-tetrahydroquinoline-8-(N-methyl)-thiocarboxamide.

10. A pharmaceutical composition as claimed in claim 1 in which the compound of formula I is 5,6,7,8-tetrahydroquinoline-8-thiocarboxamide.

11. A pharmaceutical composition as claimed in claim 1 in which the compound of formula I is 3,6-dimethyl-5,6,7,8-tetrahydroquinoline-8-thiocarboxamide or a pharmaceutically acceptable acid addition salt thereof.

12. A pharmaceutical composition as claimed in claim 1 in which the compound of formula I is 3,5-dimethyl-5,6,7,8-tetrahydroquinoline-8-thiocarboxamide or a pharmaceutically acceptable acid addition salt thereof.

13. A pharmaceutical composition as claimed in claim 1 wherein the compound of formula I is sym-octahydroacindine-4-thiocarboxamide.

14. A method of treating ulcers in an afflicted host, which method comprises orally administering to the said host a therapeutically effective amount of a compound of formula 1 as defined in claim 1.

* * * * *